(12) United States Patent
Kem

(10) Patent No.: US 10,899,822 B2
(45) Date of Patent: Jan. 26, 2021

(54) COMPOSITIONS COMPRISING D-AMINO ACID PEPTIDES AND METHODS OF PRODUCTION AND USE THEREOF FOR INHIBITING AUTOANTIBODIES

(71) Applicant: The Board of Regents of the University of Oklahoma, Norman, OK (US)

(72) Inventor: David C. Kem, Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 16/697,589

(22) Filed: Nov. 27, 2019

(65) Prior Publication Data
US 2020/0165318 A1     May 28, 2020

Related U.S. Application Data

(63) Continuation of application No. 15/995,812, filed on Jun. 1, 2018, now abandoned, which is a continuation of application No. 14/776,855, filed as application No. PCT/US2014/028362 on Mar. 14, 2014, now abandoned.

(60) Provisional application No. 61/786,758, filed on Mar. 15, 2013.

(51) Int. Cl.
| | | |
|---|---|---|
| C07K 14/72 | (2006.01) | |
| A61K 39/00 | (2006.01) | |
| A61K 38/08 | (2019.01) | |
| A61K 38/10 | (2006.01) | |
| A61K 9/00 | (2006.01) | |
| A61K 9/06 | (2006.01) | |
| A61K 9/08 | (2006.01) | |
| C07K 7/06 | (2006.01) | |

(52) U.S. Cl.
CPC .......... *C07K 14/723* (2013.01); *A61K 9/0014* (2013.01); *A61K 9/0019* (2013.01); *A61K 9/06* (2013.01); *A61K 9/08* (2013.01); *A61K 38/08* (2013.01); *A61K 38/10* (2013.01); *A61K 39/0008* (2013.01); *C07K 7/06* (2013.01)

(58) Field of Classification Search
None
See application file for complete search history.

(56) References Cited

U.S. PATENT DOCUMENTS

| 5,508,384 A * | 4/1996 | Murphy ............... C07K 14/723 |
| | | 530/324 |
| 7,745,139 B1 | 6/2010 | Wallukat et al. |
| 2005/0267207 A1 | 12/2005 | Scanlan et al. |
| 2006/0014231 A1 * | 1/2006 | Van Rompaey .......... A61P 1/02 |
| | | 435/21 |
| 2010/0135948 A1 | 6/2010 | Payne et al. |
| 2011/0263504 A1 | 10/2011 | Cerami et al. |
| 2014/0271678 A1 * | 9/2014 | Cummingham ............................ |
| | | G01N 33/56944 |
| | | 424/172.1 |
| 2014/0273015 A1 | 9/2014 | Holthoff et al. |

FOREIGN PATENT DOCUMENTS

WO     2008151847 A1     12/2008

OTHER PUBLICATIONS

Dragun, et al.; "Angiotensin II Type 1-Receptor Activating Antibodies in Renal-Allograft Rejection" The New England Journal of Medicine (2005); pp. 558-569, vol. 352, No. 6.
Wallukat, et al.; "Patients with preeclampsia develop agonistic autoantibodies against the angiotensin AT1 receptor"; The Journal of Clinical Investigation (Apr. 1999); pp. 945-952, vol. 103, No. 7.
Guichard, et al.; "Antigenic mimicry of natural L-peptides with retro-inverso-peptidomimetics"; Proceedings of the National Academy of Sciences USA (Oct. 1994); pp. 9765-9769, vol. 91, Abstract.
Scott, et al.; "Searching for Peptide Ligands with an Epitope Library"; Science, New Series (Jul. 27 1990); pp. 386-390, vol. 249, No. 4967, Abstract.
Li, et al.; "Agonistic Autoantibodies as Vasodilators in Orthostatic Hypotension: A New Mechanism"; Hypertension, originally published online (Jan. 3, 2012); pp. 402-408, vol. 59, Abstact.
International Search Report dated Jan. 14, 2015 in PCT/US2014/28362, filed Mar. 14, 2014.
Written Opinion of the International Searching Authority, dated Jan. 14, 2015 in PCT/US2014/28362, filed Mar. 14, 2014.
Grubb, Blair P.; "Postural Tachycardia Syndrome," Circulation (2008), vol. 117, pp. 2814-2817.
Raj, Satish R.; "Postural Tachycardia Syndrome (POTS)," Circulation (2013), vol. 127, pp. 2336-2342.
Sheldon, et al.; "2015 Heart Rhythm Society Expert Consensus Statement on the Diagnosis and Treatment of Postural Tachycardia Syndrome, Inappropriate Sinus Tachycardia, and Vasovagal Syncope," Heart Rhythm (2015), vol. 12, No. 6, pp. e41-e63.
Low, et al.; "Postural Tachycardia Syndrome (POTS)," Neurology (1995), vol. 45, pp. S19-S25.
Preeclampsia—Symptoms and causes—Mayo Clinic; downloaded from website www.mayoclinic.org/diseases - conditions/preeclampsia/systems-causes/syc-20355745.
Fedorowski, et al.; "Antiadrenergic Autoimmunity in Postural Tachycardia Syndrome," Europsace (2017), vol. 19, pp. 1211-1219, published online Oct. 4, 2016.
U.S. Appl. No. 14/776,855; David C. Kem, filed Sep. 15, 2015; Office Action dated Jan. 23, 2017.

(Continued)

*Primary Examiner* — Maury A Audet
(74) *Attorney, Agent, or Firm* — Dunlap Codding, P.C.

(57) ABSTRACT

Compositions are disclosed that include D-amino acid peptides and that are capable of specifically binding to at least one autoantibody against a G-protein coupled receptor. The autoantibody is produced in a patient having or being predisposed to a disease, condition, or disorder, and the autoantibody is capable of binding to a specific epitope of the G-protein coupled receptor. Methods of production and use of said compositions are also disclosed.

2 Claims, 14 Drawing Sheets

Specification includes a Sequence Listing.

(56) References Cited

OTHER PUBLICATIONS

U.S. Appl. No. 14/776,855; David C. Kem, filed Sep. 15, 2015; Amendment and Response to Office Action filed Jul. 21, 2017.
U.S. Appl. No. 14/776,855; David C. Kem, filed Sep. 15, 2015; Final Office Action dated Dec. 1, 2017.
U.S. Appl. No. 14/776,855; David C. Kem, filed Sep. 15, 2015; Response to Final Office Action dated Apr. 24, 2018.
U.S. Appl. No. 14/776,855; David C. Kem, filed Sep. 15, 2015; Advisory Action dated May 17, 2018.
U.S. Appl. No. 14/776,855; David C. Kem, filed Sep. 15, 2015; Notice of Abandonment dated Jun. 28, 2018.
U.S. Appl. No. 15/995,812; David C. Kem, filed Jun. 1, 2018; Office Action dated Jun. 27, 2019.
U.S. Appl. No. 15/995,812; David C. Kem, filed Jun. 1, 2018; Amendment and Response to Office Action dated Aug. 12, 2019.
U.S. Appl. No. 15/995,812; David C. Kem, filed Jun. 1, 2018; Office Action dated Sep. 9, 2019.

* cited by examiner

FIGURE 2
A. AT1R ECL2 Native L-Amino Acid Peptide
H₂N-Ala-Phe-His-Tyr-Glu-Ser-Gln-CONH₂
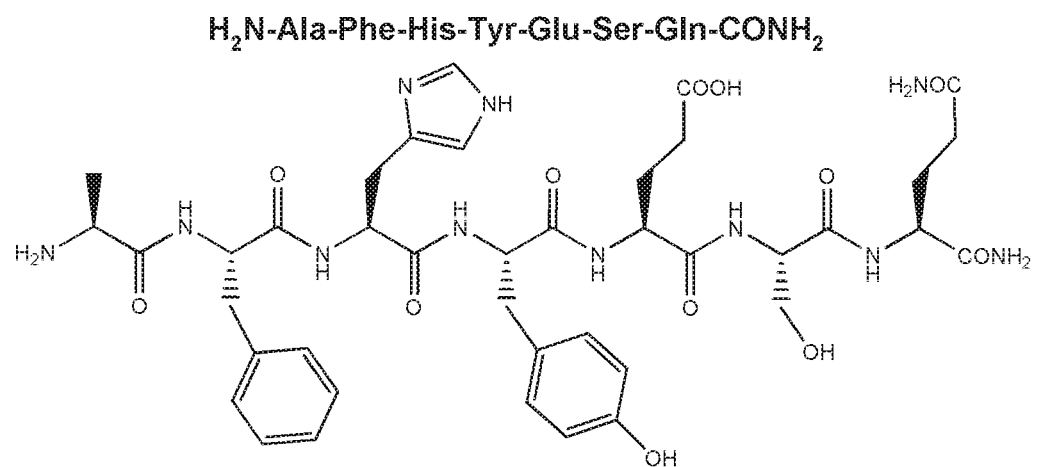
B. AT1R RID Peptide
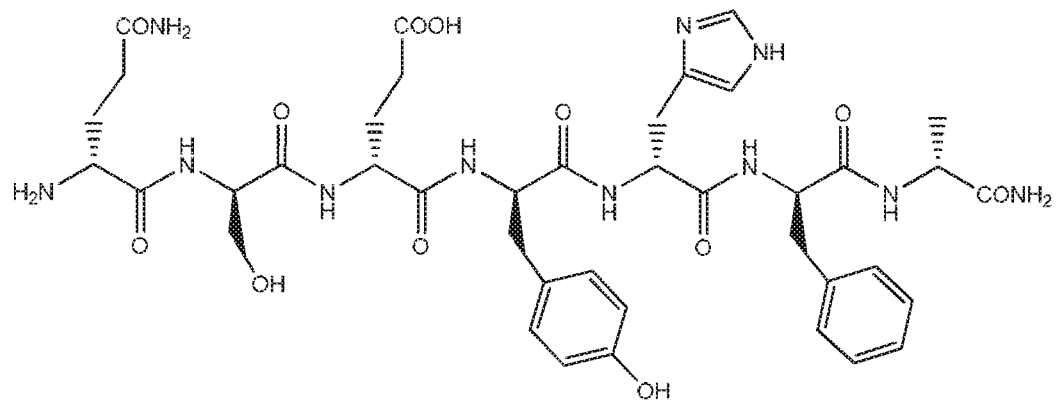

FIGURE 3
A.
AT1 peptide in vitro
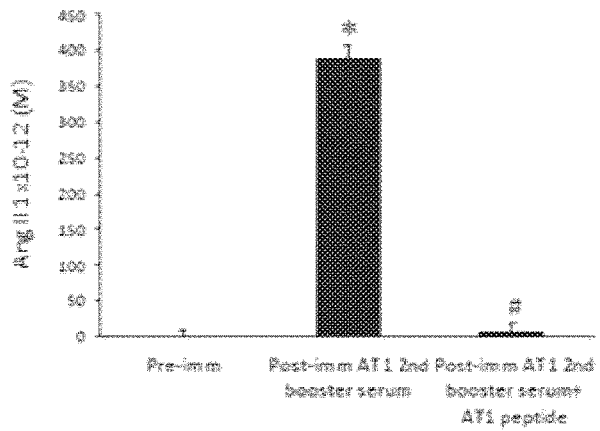
| Pre-imm. | Post-imm AT1 2nd booster serum | Post-imm AT1 2nd booster serum + AT1 peptide | |
|---|---|---|---|
| 0.49 | 339.6 | 7.5 | |
| 10.1 | 18.5 | 12.2 | Ang II 1x10-12 (M) |
B.
RID in vitro
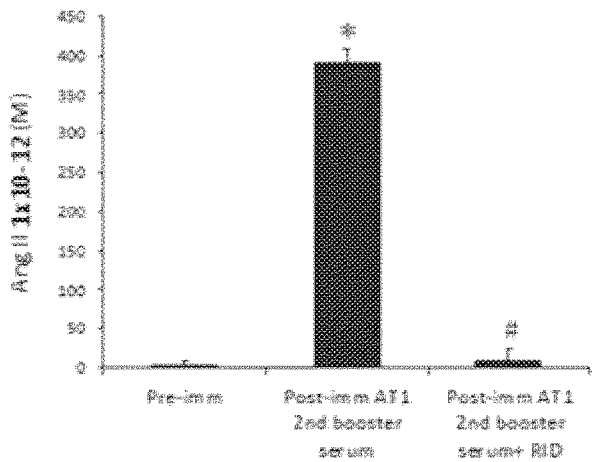
| Pre-imm. | Post-imm AT1 2nd booster serum | Post-imm AT1 2nd booster serum + RID | |
|---|---|---|---|
| 0.49 | 339.6 | 9.8 | |
| 10.1 | 18.5 | 15.2 | Ang II 1x10-12 (M) |

FIGURE 4
A.
The effect of different dilution Post-imm AT1 2$^{nd}$ booster serum on rat cremaster arterioles (42)
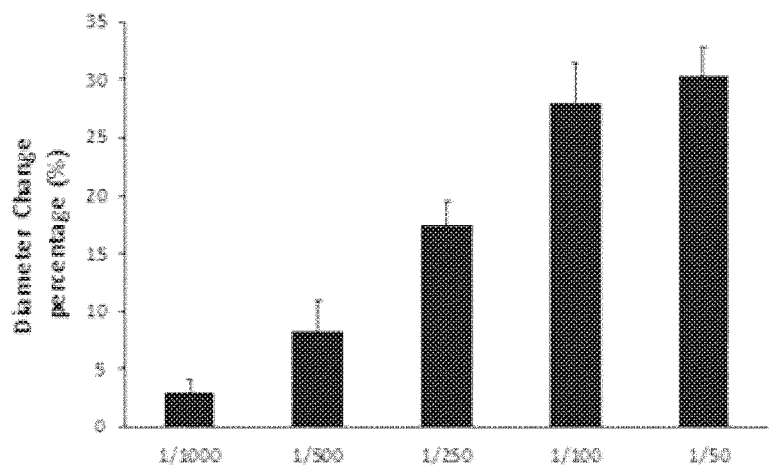
B.
Injected RID prevent Post-imm AT1 3nd booster induced vasoconstriction (1/50 in vivo)
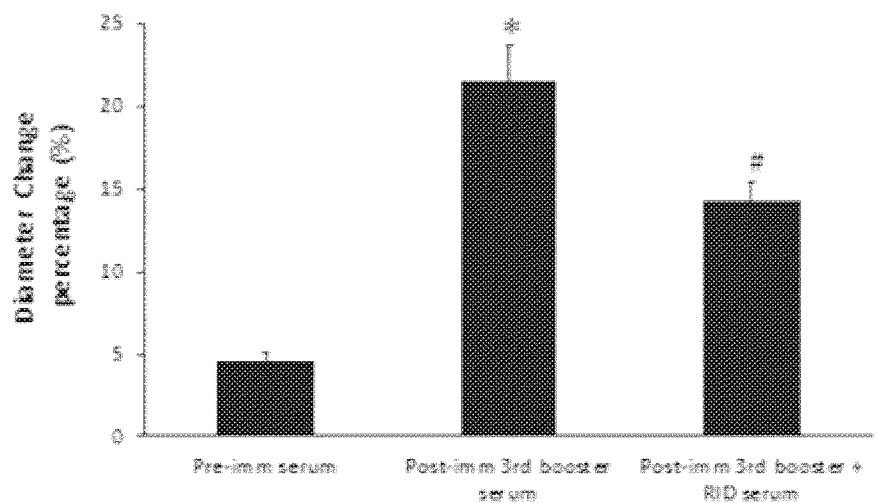

FIGURE 5
A.
Post-imm AT1 2$^{nd}$ booster rabbit Serum -induced vasoconstriction was effectively blocked by pre-incubation with RID (In vitro)
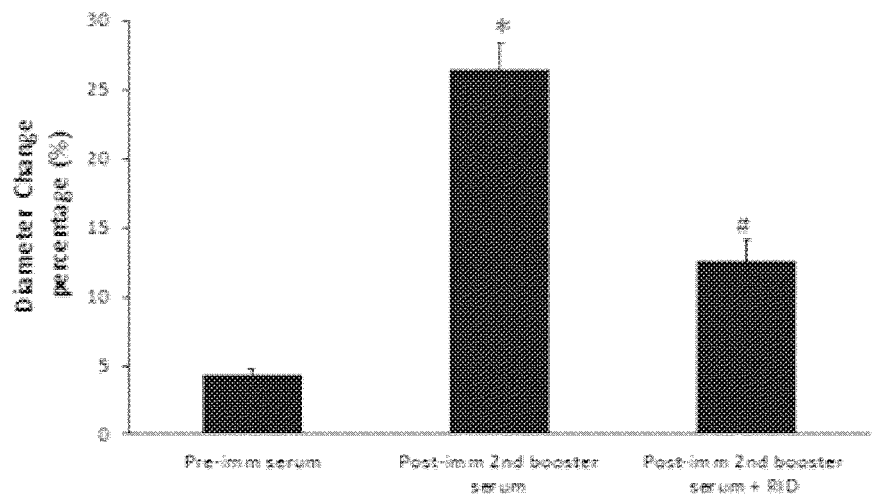
B.
Post-imm AT1 2$^{nd}$ booster rabbit Serum -induced vasoconstriction was effectively blocked by pre-incubation with AT1 peptide (In vitro).
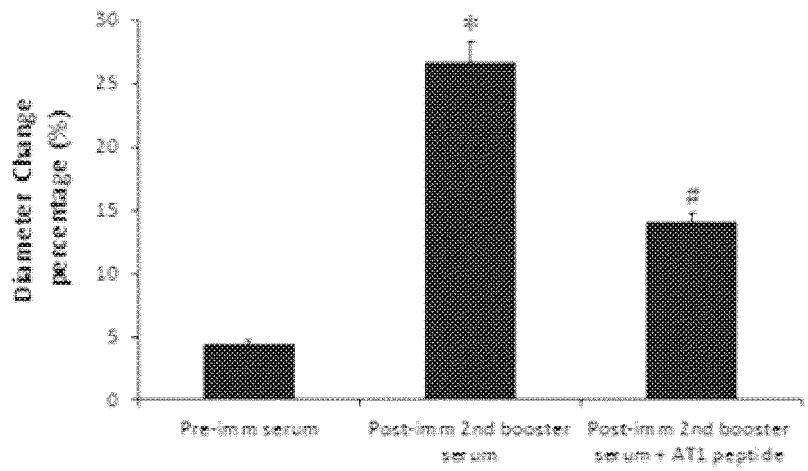

FIGURE 7
A. B1AR-ECL2 Native L-Amino Acid Peptide
H₂N-Arg-Cys-Tyr-Asn-Asp-Pro-Lys-Cys-Cys-Asp-OH
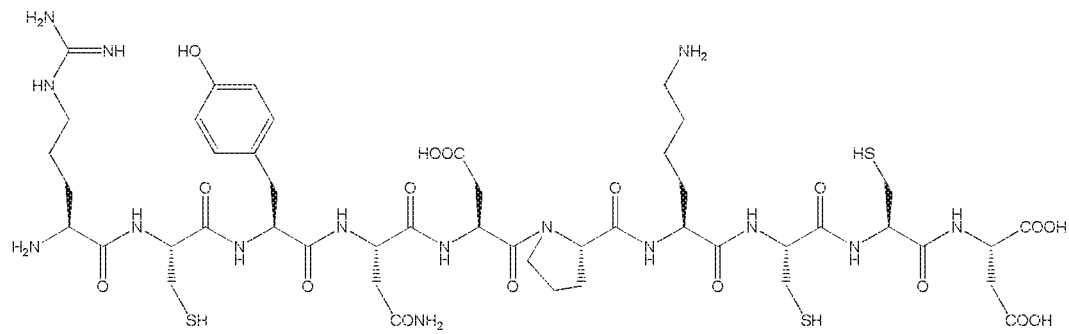
B. B1AR-ECL2 RID Peptide
H₂N-D-Asp-D-Cys-D-Cys-D-Lys-D-Pro-D-Asp-D-Asn-D-Tyr-D-Cys-D-Arg-OH
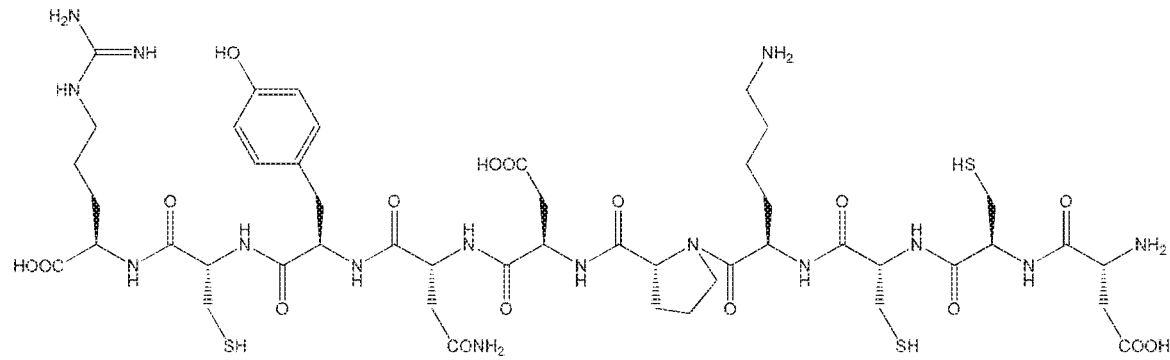

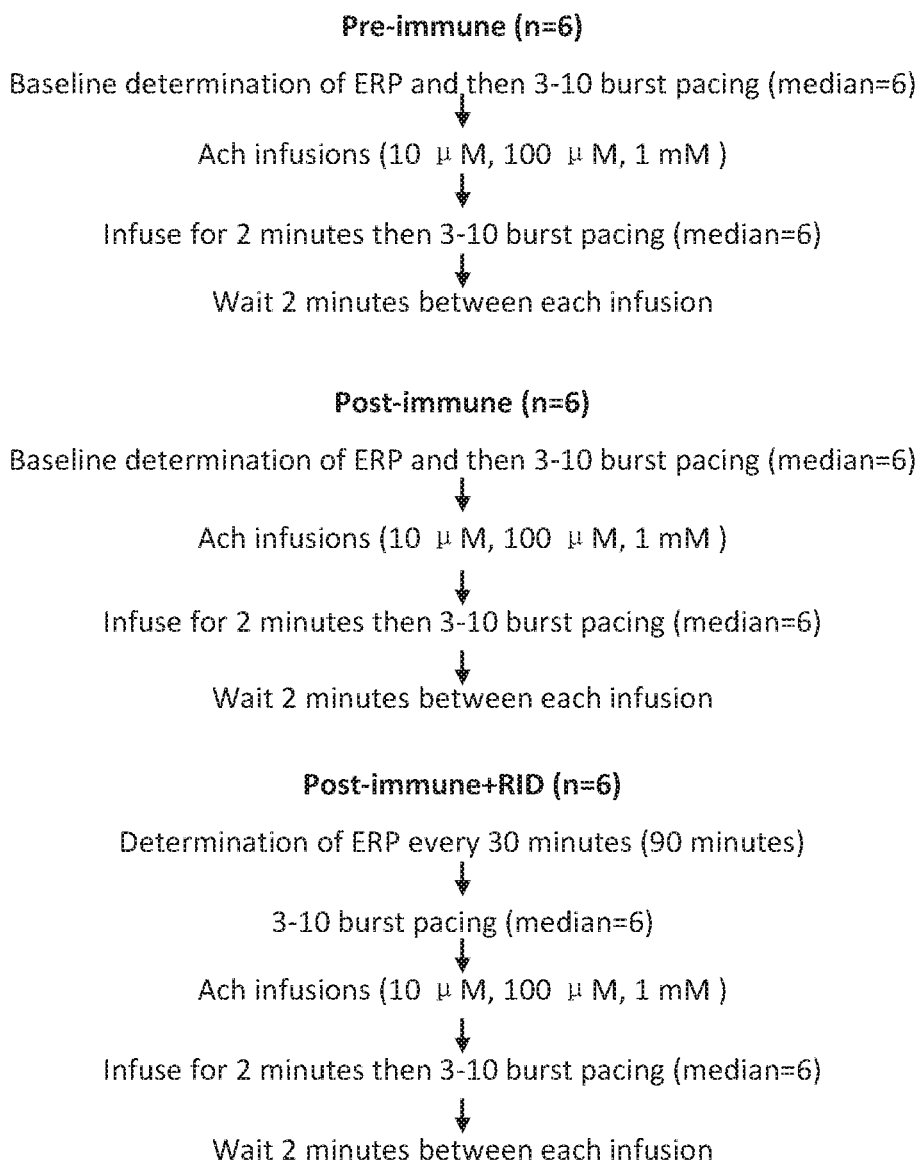

FIGURE 8

Flow Chart Depicting the Protocol of the Procedures Performed in the Rabbits

Pre-immune (n=6)

Baseline determination of ERP and then 3-10 burst pacing (median=6)
↓
Ach infusions (10 μM, 100 μM, 1 mM)
↓
Infuse for 2 minutes then 3-10 burst pacing (median=6)
↓
Wait 2 minutes between each infusion Post-immune (n=6)

Baseline determination of ERP and then 3-10 burst pacing (median=6)
↓
Ach infusions (10 μM, 100 μM, 1 mM)
↓
Infuse for 2 minutes then 3-10 burst pacing (median=6)
↓
Wait 2 minutes between each infusion Post-immune+RID (n=6)

Determination of ERP every 30 minutes (90 minutes)
↓
3-10 burst pacing (median=6)
↓
Ach infusions (10 μM, 100 μM, 1 mM)
↓
Infuse for 2 minutes then 3-10 burst pacing (median=6)
↓
Wait 2 minutes between each infusion FIGURE 12
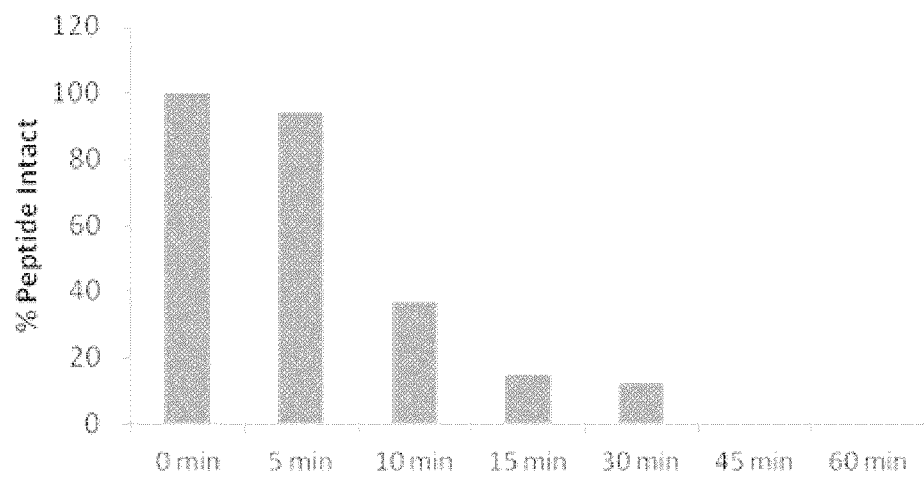
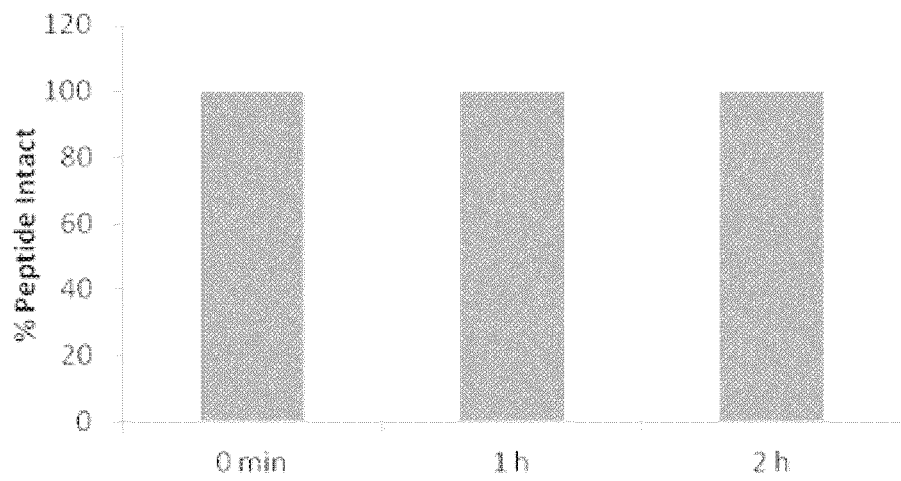

FIGURE 13
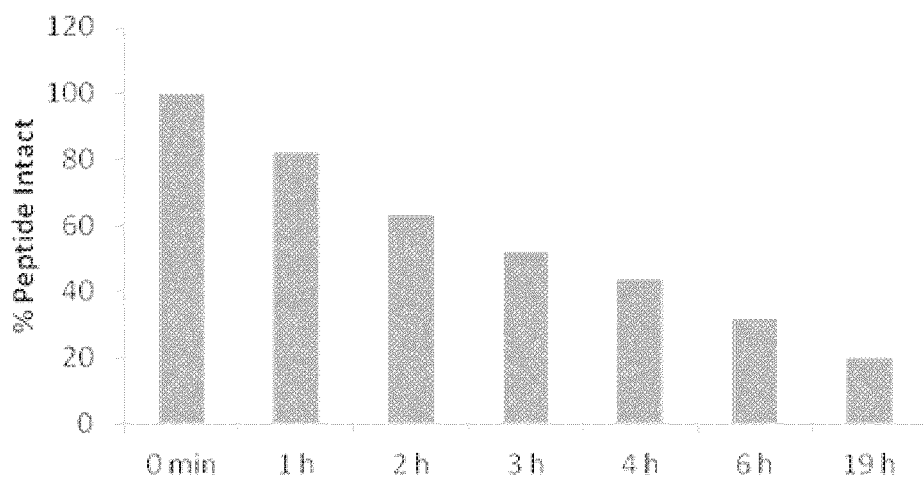
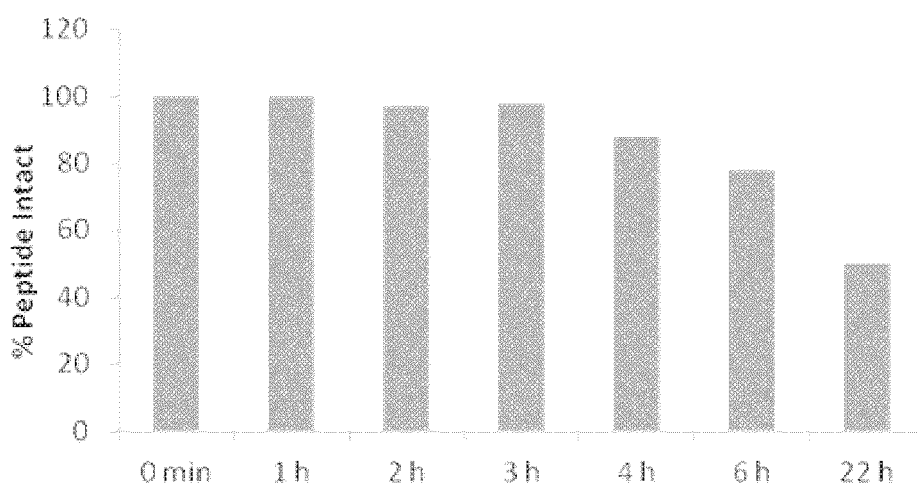

FIGURE 15
A. B2AR-ECL2 Native L-Amino Acid Peptide
H₂N-His-Trp-Tyr-Arg-Ala-Thr-OH
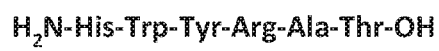
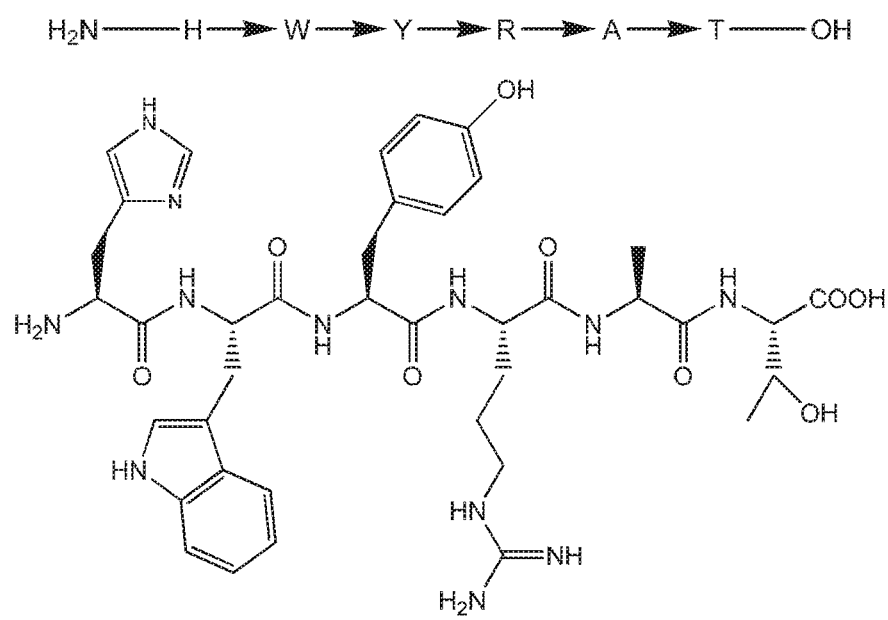
B. B2AR-ECL2-RID Peptide
H₂N-D-Thr-D-Ala-D-Arg-D-Tyr-D-Trp-D-His-OH
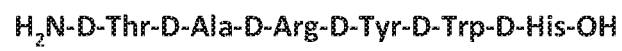
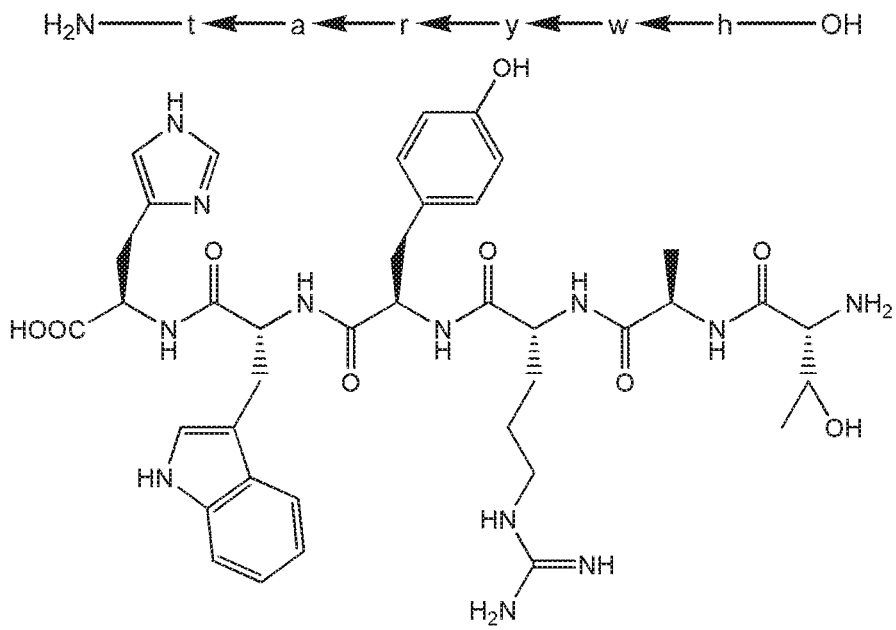

COMPOSITIONS COMPRISING D-AMINO ACID PEPTIDES AND METHODS OF PRODUCTION AND USE THEREOF FOR INHIBITING AUTOANTIBODIES

CROSS REFERENCE TO RELATED APPLICATIONS/INCORPORATION BY REFERENCE STATEMENT

This application is a continuation of U.S. Ser. No. 15/995,812, filed Jun. 1, 2018, now abandoned; which is a continuation of U.S. Ser. No. 14/776,855, filed Sep. 15, 2015, now abandoned; which is a US national stage application filed under 35 USC § 371 of International Application No. PCT/US2014/028362, filed Mar. 14, 2014; which claims priority under 35 USC § 119(e) of provisional application U.S. Ser. No. 61/786,758, filed Mar. 15, 2013. The entire contents of the above-referenced patent applications are hereby expressly incorporated herein by reference.

STATEMENT REGARDING FEDERALLY SPONSORED RESEARCH OR DEVELOPMENT

Not Applicable.

BACKGROUND

A large number of patients have circulating autoantibodies directed toward specific receptors (for example, but not by way of limitation, G-protein coupled receptors (GPCR)) which activate or partially block their function and are causative of a wide variety of symptoms and abnormal bodily functions. Although specific pharmacological blockade is presently available and may provide partial relief, these agents generally block the receptor rather than just the autoantibody. This receptor blockade is frequently only partially effective and/or can even make the symptoms worse, since they do not block the site which is directly targeted by the antibody within the receptor complex. It is known that a target peptide can be used to provide short term blockade of the autoantibody, but the very rapid inactivation of these target-peptides within the body makes it difficult to use them for treatment. Cyclic peptides (constructed with L-amino acid components) which are effective in blocking antibody function are known (see U.S. Pat. No. 8,187,605); however, these cyclic peptides involve complex synthetic processes. Thus, alternate peptide structures which have prolonged and effective biological activity in vivo, and which do not interfere with necessary receptor responsivity to normal receptor stimuli, are desirable. Therefore, the presently disclosed inventive concepts are directed to compositions containing new peptide structures that overcome the disadvantages and defects of the prior art, as well as methods of production and use thereof, along with kits containing same.

BRIEF DESCRIPTION OF THE DRAWINGS

FIG. 2 illustrates the peptide structures of an epitope and its corresponding RID peptide constructed in accordance with the presently disclosed inventive concepts. The top peptide structure is of the angiotensin type 1 receptor (AT1R) $2^{nd}$ extracellular loop (ECL2) L-amino acid epitope (AFHYESQ; SEQ ID NO:2) that is the target "epitope" for the activating autoantibody directed toward the AT1R. The bottom peptide structure is of the retro-inverso D-amino acid (RID) peptide (qseyhfa; SEQ ID NO:4) that has been constructed in accordance with the presently disclosed inventive concepts and is based on the native L-amino acid sequence shown in the top peptide structure. The RID peptide serves as a "decoy" target for the activating autoantibodies because of its structural similarity to the native epitope.

FIG. 3 illustrates the in vitro effects of pre-immune (pre-imm), AT1R post-immune (post-imm) and AT1R post-immune serum incubated with the native AT1R $2^{nd}$ ECL peptide (FIG. 3, Panel A) on activation of AT1R transfected CHO cells. The data are expressed as Ang II equivalent values. There are minimal effects from the pre-immune sera, a marked increase in activity from the rabbit sera containing the autoantibodies to the $2^{nd}$ ECL epitope, and significant inhibition of activation in the identical rabbit sera when pre-incubated with either the native L-amino acid peptide (FIG. 3, Panel A) or the RID peptide (FIG. 3, Panel B). There is no significant difference between the effects of the native peptide and the RID decoy peptide.

FIG. 4, Panel A illustrates the dose related contractile effect of serum from an AT1R $2^{nd}$ ECL peptide immunized rabbit on an isolated rat cremaster artery. The in vitro contractile changes were expressed as % change (decrease) in diameter with the increasing dosage concentration (dilution). These effects are blocked by the selective angiotensin II receptor blocker (ARB) losartan.

FIG. 4, Panel B shows the effects of serum taken from the same animals as in Panel A of FIG. 4 in the pre-immune, post-immune, and post immune+RID peptide (2 mg/Kg iv) for 90 minutes. There was a significant increase of in vitro cremaster contractility (p<0.01) in the post-immune state compared to the pre-immune values. There was a significant decrease in activity in the post-immune serum contractility 90 minutes after administration of the decoy RID peptide (p<0.05). A similar effect is observed with the native L-amino acid $2^{nd}$ ECL peptide (data not included).

FIG. 5 illustrates the effect of in vitro incubation of the RID peptide with serum containing AT1R activating autoantibodies (rabbit) on cremaster artery contractility. The post-immunized rabbit sera markedly increased contractility (p<0.01). After 2 hrs pre-incubation with the decoy RID peptide, these same sera had significantly lesser contractile activity (FIG. 5, Panel A, p<0.05). The same response was observed when the serum was pre-incubated with the L-amino acid target peptide (FIG. 5, Panel B). These data demonstrate that the enzyme-resistant RID peptide has virtually identical affinity for the autoantibody as has its short lived L-amino acid target peptide.

FIG. 7 illustrates another embodiment of a RID peptide constructed in accordance with the presently disclosed inventive concepts. The top peptide structure is of the β1AR ECL2 L-amino acid epitope (RCYNDPKCCD; SEQ ID NO:26) that is the target for activating autoantibodies to the β1AR in humans. The bottom peptide structure is of the retro-inverso D-amino acid (RID) peptide (dcckpdnycr; SEQ ID NO:27) that has been constructed in accordance with the presently disclosed inventive concepts and is based on the native L-amino acid sequence shown in the top peptide structure. The RID peptide serves as a "decoy" target for the activating autoantibody to the β1AR.

FIG. 8 contains a flow chart depicting the protocol of the procedures performed in rabbits in a study to determine the effective refractory period (ERP) in atrial cells in rabbit-models with pre-immune, post-immune (β1AR-immunization), and post-immune plus β1AR-ECL2 RID peptide administration. The ERP inversely is one parameter of the susceptibility of the cardiac cells to induction of tachyarrhythmias.

FIG. 12 graphically illustrates an in vitro stability analysis of the native and RID peptides in human serum at 37° C., as measured by HPLC. This Figure indicates the rapid rate of in vitro proteolysis (within 30 minutes) of the AT1R-ECL2 L-amino acid peptide and the resistance of the AT1R-ECL2 RID peptide to proteolysis after two hours. In addition, 80% of the RID peptide remained after 24 hours (data not shown).

FIG. 13 graphically illustrates an in vitro stability analysis of the native and RID peptides in synthetic gastric fluid (SGF, pepsin+HCL, pH 1.2) at 37° C., as measured by HPLC. This Figure indicates the rate of proteolysis of the AT1R-ECL2 L-amino acid peptide and the AT1R-ECL2 RID peptide under these conditions. A similar resistance of the AR1R-ECL2 RID peptide was observed in synthetic pancreatic fluid containing trypsin at pH 6.3 (data not shown).

FIG. 15 illustrates another embodiment of a RID peptide constructed in accordance with the presently disclosed inventive concepts. The top peptide structure is of the β2AR ECL2 L-amino acid epitope (HWYRAT; SEQ ID NO:28) that is the target for activating autoantibodies. The bottom peptide structure is of the retro-inverso D-amino acid (RID) peptide (tarywh; SEQ ID NO:29) that has been constructed in accordance with the presently disclosed inventive concepts and is based on the native L-amino acid sequence shown in the top peptide structure. The RID peptide serves as a "decoy" target for the activating autoantibodies.

DETAILED DESCRIPTION

Figure 1:
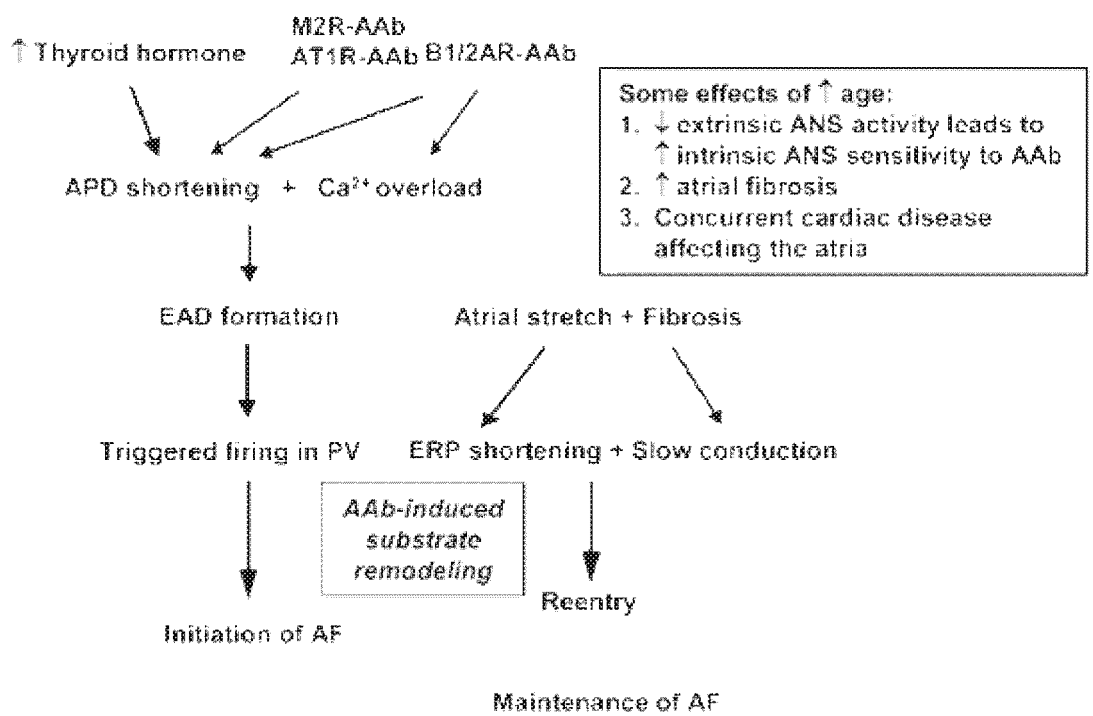
FIG. 1 graphically depicts the proposed interactive effects of thyroid hormone, activating autoantibodies (AAb), and increasing age on one type of atrial fibrillation. This represents but one of many proposed interactions of AAb with cardiac arrhythmias alone. This concept is also possible for the impact of these and other GPCR-AAb targets in other tissues/organs in the body of living organisms.

Before explaining the at least one non-limiting embodiment of the inventive concepts disclosed herein in detail, it is to be understood that the presently disclosed inventive concepts is not limited in its application to the details of examples, experiments, exemplary data, and/or methods or steps as set forth in the following description, or illustrated in the drawings. The presently disclosed inventive concepts are capable of other embodiments or of being practiced or carried out in various ways. Also, it is to be understood that the phraseology and terminology employed herein is for purpose of description only and should not be regarded as limiting in any way unless specifically indicated as such.

In the following detailed description of embodiments of the presently disclosed inventive concepts, numerous specific details are set forth in order to provide a more thorough understanding of the inventive concepts. However, it will be apparent to one of ordinary skill in the art that the inventive concepts within the disclosure may be practiced without these specific details. In other instances, well-known features have not been described in detail to avoid unnecessarily complicating the present disclosure.

Unless otherwise defined herein, scientific and technical terms used in connection with the presently disclosed inventive concepts shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2nd ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

All patents, published patent applications, and non-patent publications mentioned in the specification are indicative of the level of skill of those skilled in the art to which this presently disclosed inventive concepts pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions and/or methods disclosed and claimed herein can be made and executed without undue experimentation in light of the present disclosure. While the compositions and methods of this invention have been described in terms of particular embodiments, it will be apparent to those of skill in the art that variations may be applied to the compositions and/or methods and in the steps or in the sequence of steps of the method described herein without departing from the concept, spirit, and scope of the invention. All such similar substitutes and modifications apparent to those skilled in the art are deemed to be within the spirit, scope, and concept of the inventive concepts as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." The term "plurality" refers to "two or more". Throughout this application, the term "about" is used to indicate that a value includes the inherent variation of error for the device, the method being employed to determine the value, or the variation that exists among the study subjects. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

Throughout the specification and claims, unless the context requires otherwise, the terms "substantially" and "about" will be understood to not be limited to the specific terms qualified by these adjectives/adverbs, but will be understood to indicate a value includes the inherent variation of error for the device, the method being employed to determine the value and/or the variation that exists among study subjects. Thus, said terms allow for minor variations and/or deviations that do not result in a significant impact thereto. For example, in certain instances the term "about" is used to indicate that a value includes the inherent variation of error for the device, the method being employed to determine the value and/or the variation that exists among study subjects; alternatively, the term "about," herein when referring to a measurable value such as an amount, a temporal duration, and the like, is meant to encompass variations of ±20% or ±10%, or ±5%, or ±1%, or ±0.1% from the specified value, as such variations are appropriate to perform the disclosed methods and as understood by persons having ordinary skill in the art. Similarly, the term "substantially" may also relate to 80% or higher, such as 85% or higher, or 90% or higher, or 95% or higher, or 99% or higher, and the like.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, "pharmaceutically acceptable" refers to those properties and/or substances, which are acceptable to the patient from a pharmacological/toxicological point of view including bioavailability and patient acceptance or to the manufacturing chemist from a physical-chemical point of view regarding composition, formulation, stability and isolatability. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically-acceptable carrier" as used herein means a pharmaceutically-acceptable material, composition, or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

By "biologically active" is meant the ability to modify the physiological system of an organism. A molecule can be biologically active through its own functionalities, or may be biologically active based on its ability to activate or inhibit molecules having their own biological activity.

As used herein, "substantially pure" means an object species is the predominant species present (i.e., on a molar basis it is more abundant than any other individual species in the composition), and particularly a substantially purified fraction is a composition wherein the object species comprises at least about 50 percent (on a molar basis) of all macromolecular species present. Generally, a substantially pure composition will comprise more than about 80 percent of all macromolecular species present in the composition, such as more than about 85%, 90%, 95%, and 99%. In one embodiment, the object species is purified to essential homogeneity (contaminant species cannot be detected in the composition by conventional detection methods) wherein the composition consists essentially of a single macromolecular species.

The term "patient" as used herein includes human and veterinary subjects. "Mammal" for purposes of treatment refers to any animal classified as a mammal, including human, domestic and farm animals, nonhuman primates, and any other animal that has mammary tissue.

"Treatment" refers to both therapeutic treatment and prophylactic or preventative measures. Those in need of treatment include, but are not limited to, individuals already having a particular condition or disorder as well as individuals who are at risk of acquiring a particular condition or disorder (e.g., those needing prophylactic/preventative measures). The term "treating" refers to administering an agent to a patient for therapeutic and/or prophylactic/preventative purposes.

A "therapeutic composition" or "pharmaceutical composition" refers to an agent that may be administered in vivo to bring about a therapeutic and/or prophylactic/preventative effect.

Administering a therapeutically effective amount or prophylactically effective amount is intended to provide a therapeutic benefit in the treatment, reduction in occurrence, prevention, or management of a disease and/or cancer. The specific amount that is therapeutically effective can be readily determined by the ordinary medical practitioner, and can vary depending on factors known in the art, such as the type of disease/cancer, the patient's history and age, the stage of disease/cancer, and the co-administration of other agents.

A "disorder" is any condition that would benefit from treatment with the polypeptide. This includes chronic and acute disorders or diseases including those pathological conditions which predispose the mammal to the disorder in question.

The terms "cancer" and "cancerous" refer to or describe the physiological condition in mammals that is typically characterized by unregulated cell growth. Examples of cancers include, but are not limited to, carcinoma, lymphoma, blastoma, sarcoma, and leukemia. More particular examples of such cancers include squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer.

The term "effective amount" refers to an amount of a biologically active molecule or conjugate or derivative thereof sufficient to exhibit a detectable therapeutic effect without undue adverse side effects (such as toxicity, irritation and allergic response) commensurate with a reasonable benefit/risk ratio when used in the manner of the inventive concepts. The therapeutic effect may include, for example but not by way of limitation, inhibiting the growth of undesired tissue or malignant cells. The effective amount for a subject will depend upon the type of subject, the subject's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

As used herein, the term "concurrent therapy" is used interchangeably with the terms "combination therapy" and "adjunct therapy", and will be understood to mean that the patient in need of treatment is treated or given another drug for the disease in conjunction with the pharmaceutical compositions of the presently disclosed inventive concepts. This concurrent therapy can be sequential therapy, where the patient is treated first with one drug and then the other drug, or the two drugs can be given simultaneously.

The terms "administration" and "administering" as used herein will be understood to include all routes of administration known in the art, including but not limited to, oral, topical, transdermal, parenteral, subcutaneous, intranasal, mucosal, intramuscular, intraperitoneal, intravitreal and intravenous routes, including both local and systemic applications. In addition, the compositions of the presently disclosed inventive concepts (and/or the methods of administration of same) may be designed to provide delayed, controlled or sustained release using formulation techniques which are well known in the art.

The presently disclosed inventive concepts also include a pharmaceutical composition comprising a therapeutically effective amount of at least one of the compositions described herein in combination with a pharmaceutically acceptable carrier. As used herein, a "pharmaceutically acceptable carrier" is a pharmaceutically acceptable solvent, suspending agent or vehicle for delivering the compositions of the presently disclosed inventive concepts to the human or animal. The carrier may be liquid or solid and is selected with the planned manner of administration in mind. Examples of pharmaceutically acceptable carriers that may be utilized in accordance with the presently disclosed inventive concepts include, but are not limited to, PEG, liposomes, ethanol, DMSO, aqueous buffers, oils, DPPC, lipids, other biologically-active molecules, vaccine-adjuvants, and combinations thereof.

As used herein, a "therapeutically effective amount" of the inhibitor or chemotherapeutic agent of the presently disclosed inventive concepts refers to an amount of a compound that is effective, upon single- or multiple-dose administration to the subject, e.g., a patient, at treating, inhibiting, mitigating, reducing, modulating, or otherwise affecting any of the disorders, diseases, or conditions described elsewhere herein, for example, orthostatic hypotension, or any other condition involving a disorder, disease or condition which involves autoantibodies to any of the receptors described herein.

While the presently disclosed inventive concepts will now be described in connection with certain embodiments in the following examples so that aspects thereof may be more fully understood and appreciated, it is not intended to limit the invention to these particular examples. On the contrary, it is intended to cover all alternatives, modifications and equivalents as may be included within the scope of the presently disclosed inventive concepts as defined herein and in the appended claims. Thus, the following examples, which include particular embodiments will serve to illustrate the practice of the presently disclosed inventive concepts, it being understood that the particulars shown are by way of example and for purposes of illustrative discussion of particular embodiments of the presently disclosed inventive concepts only and are presented in the cause of providing what is believed to be the most useful and readily understood description of compounds, methods of use, and formulation procedures as well as of the principles and conceptual aspects of the presently disclosed inventive concepts.

Turning now to the presently disclosed inventive concepts, compositions are described herein that include at least one D-amino acid peptide, and in certain embodiments, at least one retro-inverso D-amino acid (RID) peptide. Particular D-amino acid-containing peptides that may be utilized in accordance with the presently disclosed inventive concepts will be defined in detail in later portions of this disclosure. The peptides are capable of specifically binding to autoantibodies, and in particular, to autoantibodies produced in a patient having (or predisposed to) a disease, condition, and/or disorder. In certain embodiments, the peptides may be capable of specifically binding to autoantibodies that either activate or block G-protein coupled receptors.

The presently disclosed inventive concepts include an inhibitory composition comprising any of the D-amino acid (D-aa) peptides described or otherwise contemplated herein.

The presently disclosed inventive concepts also include a pharmaceutical composition comprising a therapeutically effective amount of at least one of the peptides described or otherwise contemplated herein, in combination with a pharmaceutically acceptable carrier.

The presently disclosed inventive concepts further include a method of decreasing the binding of an autoantibody to a target receptor. In the method, the autoantibody is contacted with any of the compositions described or otherwise contemplated herein, whereby the D-amino acid-containing peptide(s) present in the composition bind to the autoantibody and prevent it from binding to its target receptor.

The presently disclosed inventive concepts further include a method of reducing the occurrence and/or severity of a disease/disorder. In the method, any of the compositions described or otherwise contemplated herein is administered to a patient experiencing (or predisposed to) the disease/disorder.

The presently disclosed inventive concepts are further directed to methods of administering any of the compositions described or otherwise contemplated herein for treatment in the various disorders, conditions, and diseases described herein which involve any of the G-protein coupled receptors described herein.

The use of the L-amino acid peptide epitope to block autoantibodies has been considered within the prior art; however, these naturally-occurring peptides have not been effectively applicable because of their short survival time in vivo. The use of the cyclic structure described by Jahns et al. (Circulation (2005) 112(Suppl. II:5):120) appears to be useful; however, the synthesis requirements of this construct are significantly more complicated than for the construct of the presently disclosed inventive concepts, as an entirely different means of protection of the cyclic peptide structure is utilized; in addition, IV infusion is required for administration of the peptides of Jahns et al. The synthesis of the D-amino acid-containing peptide described herein can be adapted to a very large number of circumstances wherein autoimmune diseases have a specific identifiable target epitope; in addition, these D-amino acid-containing peptides are amenable to oral administration and use because of their small size and inherent protection from proteolytic degradation by gastric and intestinal enzymes. The small size of these peptides makes them amenable to penetrating certain partially impermeable membranes in the mammalian body, including the aforesaid gastrointestinal barrier but also not excluding the central blood brain and the renal glomerular barrier.

In particular, the present D-amino acid-containing peptides are applicable specifically to use in diseases of man and animal that are based on autoantibodies that either activate or block G-protein coupled receptors. This same use of a decoy peptide is also applicable to other diseases wherein other autoantibodies not necessarily "activating" in nature are directed toward various cells in the body, and their specific targeted epitope has been identified. The presently disclosed inventive concepts include, for example but not by way of limitation, D-amino acid-containing peptides (including, but not limited to, RID peptides) based on the epitope structure of the Angiotensin II type 1 receptor (AT1R), the adrenergic receptors β1AR and β2AR, the muscarinic acetylcholine receptors M2R and M3R, α1 autonomic receptor (α1AR), and the dopamine receptors D1R and D2R receptors. In certain embodiments, the D-amino acid-containing peptides are based on at least a portion of an epitope positioned with an extracellular loop (such as, but not limited to, ECL1 and ECL2) of these receptors. The presently disclosed inventive concepts also include target peptide(s) specific for other GPCR-directed autoantibodies, such as but not limited to, the thyroid stimulating hormone receptor (TSHR), β3-adrenergic receptor (β3AR), an endothelin receptor(s), a thrombin receptor(s), and orphan GPCR's whose function has yet to be determined. Further, according to the presently disclosed inventive concepts, for any given epitope, a D-amino acid-containing peptide can be constructed as described herein which will provide at least equivalent blocking activity for the specific autoantibody to which it is directed toward, thereby decreasing the ability of the autoantibody to bind to a target receptor.

In accordance with the presently disclosed inventive concepts, non-limiting examples of construction of antibody-blocking peptides are explained herein below. The following terminology is used: ECL1 and ECL2 refer to human receptor peptide sequences of the 1st and 2nd extracellular loops of G-protein coupled receptors. TMD refers to the generally conserved sequences known as trans membrane domains of the receptors located upstream and downstream of the loop sequences (wherein the loop sequences without the TMD portion are designated as SEQ ID NOs: 1 and 5-18 below). L-amino acids are shown in UPPER CASE. D-amino acids are shown in lower case. Table 1 contains portions of the sequences of GPCRs on which the D-amino acid-containing peptides may be based; underlined sequences refer to known functional epitopes (binding epitope) for potential and documented receptor activity target sites for autoantibodies.

TABLE 1

| GPCR Target Site | Sequence | SEQ ID NO: |
|---|---|---|
| AT1R ECL2 | (TMD)- IHRNVFFIENTNITVC<u>AFHYESQ</u>NSTL -(TMD) | 1 |
| β1AR ECL1 | (TMD)- WGRWEYGSFFCEL -(TMD) | 5 |
| β1AR ECL2 | (TMD)- HWWRAESDEARRCYNDPKCCDFVTNR -(TMD) | 6 |
| β2AR ECL1 | (TMD)- MKMWTFGNFWC -(TMD) | 7 |
| β2AR ECL2 | (TMD)- <u>HWYRATHQEAINCYANETCCDFFTNQ</u> -(TMD) | 8 |
| D1 ECL2 | (TMD)- HKAKPTSPSDGNATSLAETIDNCDSSLSR -(TMD) (aa's 164-192) | 9 |
| D2 ECL2 | (TMD)- GLNNADQNECIIANPA -(TMD) (aa's 173-188) | 10 |

TABLE 1-continued

| GPCR Target Site | Sequence | SEQ ID NO: |
|---|---|---|
| M2R ECL1 | (TMD)- TLYTVIGYWPLGPVVCD -(TMD) | 11 |
| M2R ECL2 | (TMD)- VRTVEDGECYIQFFSNAAVTFGTAI -(TMD) | 12 |
| M3R ECL1 | (TMD)- TTYIIMNRWALGNLACD -(TMD) | 13 |
| M3R ECL2 | (TMD)- KRTVPPGECFIQFLSEPTITFGTAI -(TMD) | 14 |
| α1AR ECL1 | (TMD)- YWAFGRVFCNIWA -(TMD) | 15 |
| α1AR ECL2 | (TMD)- GWRQPAPEDETICQINEEPGYVLFS -(TMD) | 16 |
| AT1R ECL1 | (TMD)- TAMEYRWPFGNYLCK -(TMD) | 17 |
| AT2R ECL2 | (TMD)- YFRDVRTIEYLGVNACIMAFPPEKYAQWS -(TMD) (aa's 180-208) | 18 |

L-amino acids ("L-AA") comprise the natural autoantibody-targeted $1^{st}$, $2^{nd}$, or $3^{rd}$ extracellular loops (ECL) of G-protein coupled receptors (GPCR's). Table 1 lists a representative but not exclusive listing of such targets associated with autoantibody-activated pathophysiological conditions. The native peptide has a target structure representing the sequence:

(Upstream TMD)-kX•EPITOPE•kY-(Downstream TMD), wherein kX represents the amino acids between the upstream TMD and the autoantibody-binding epitope of the receptor, and wherein kY represents the amino acids between the downstream TMD and the autoantibody-binding epitope of the receptor. EPITOPE refers to the defined or suspected amino acid sequence of the receptor to which the autoantibody binds and usually comprises 4-7 amino acids. The specific binding epitope of the kX-EPITOPE-kY sequence may be known or unknown. In a particular embodiment the RID peptide comprises D-amino acid substitutions of at least five of the L-amino acids of the EPITOPE portion of the receptor, and particularly the at least five central-most residues of the EPITOPE. For example where an EPITOPE comprises 7 L-amino acids, the RID peptide would comprise D-amino acids at least corresponding to amino acid positions 2-6 of the EPITOPE.

In accordance with the presently disclosed inventive concepts, a peptide is constructed in a retro-inverso fashion (alternative nomenclature: retro-enantio peptide) using D-amino acids in place of the natural L-amino acids from any of the loop sequences defined above. This peptide construction is based on an amino acid sequence orientation represented as:

(Downstream TMD)-yk•epitope•xk-(upstream TMD).

Figure 6:
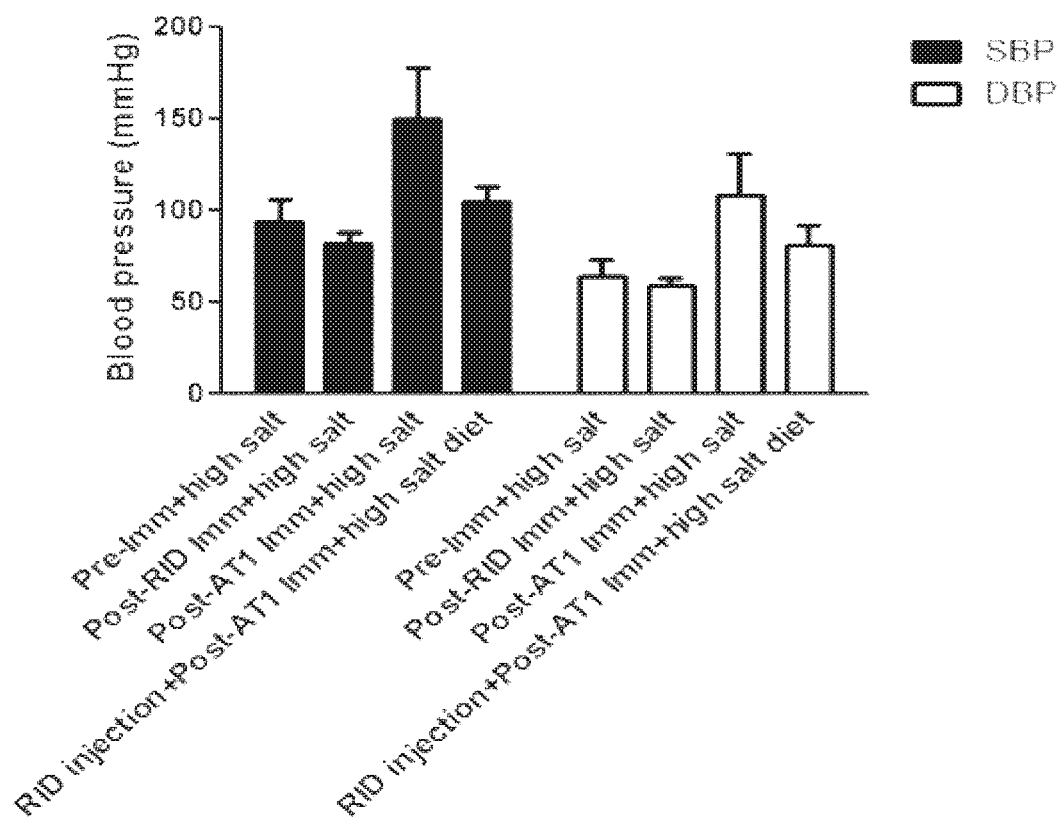
FIG. 6 illustrates the effects of the AT1R-ECL2 RID peptide on blood pressure BP) in a rabbit model of hypertension. The AT1R-ECL2 RID peptide had not significant effect on BP in the pre-immune state but produced a significant drop in systolic and diastolic BP in the post-immune state.

The RID peptide does not include the TMD structures but only amino acids selected from the sequence "yk•epitope•xk", wherein the amino acids are in reverse order as compared to the native sequence "kX•EPITOPE•kY", such that the carboxy-terminal residue now appears in the place of the upstream amino-terminal residue and the amino-terminal residue now appears in the place of the downstream carboxy-terminal residue (see, for example, FIG. 2 or 6). In this peptide structure, the side chain structures are positioned in a manner analogous to those expressed in the original structure, but the peptide contains (and in one non-limiting embodiment, may consist entirely of) D-amino acids that are resistant to proteolysis in mammals, including humans.

In one embodiment, the RID peptide is derived from the full sequence of an extracellular loop of a GPCR. For example but not by way of limitation, the RID peptide may be derived from the AT1R ECL, wherein the underlined portion below represents the known autoantibody targeted peptide epitope. In this example, the RID peptide is derived from the entire known autoantibody ECL sequence comprising the target epitope within its broad structure.

```
Natural sequence:
                                        (SEQ ID NO: 1)
(upstream-TMD)- IHRNVFFIENTNITVCAFHYESQNSTL-
(downstream-TMD)

Full retro/inverso D-aa (RID) sequence:
                                        (SEQ ID NO: 3)
ltsnqseyhfacvtintneiffvnrhi.
```

In another embodiment, the RID peptide is based on only the specific autoantibody-binding epitope of the GPCR. The RID peptide side groups present as a mirror image of its L-AA enantiomer; however, the opposite side of this same RID peptide consequentially presents as the similar side chain as its L-AA enantiomer.

In the non-limiting example of the AT1R ECL, the natural sequence and RID peptide are as follows:

```
                                        (SEQ ID NO: 2)
        Natural sequence: AFHYESQ (SEQ ID NO: 4)
        RID sequence: qseyhfa.
```

In the non-limiting example of the D1R ECL2, the natural sequence and its RID peptide are as follows:
Natural sequence: HKAKPTSPSDGNATSLA-ETIDNCDSSLSR (SEQ ID NO:9)
RID sequence: rslssdcnditealstangdspstpkakh (SEQ ID NO:30).

In the non-limiting example of the D2R ECL2, the natural sequence and its RID peptide are as follows:
Natural sequence: GLNNADQNECIIANPA (SEQ ID NO:10)
RID sequence: apnaiicenqdannlg (SEQ ID NO:31).

In another embodiment, the RID peptide is constructed based on a subportion of the full RID sequence, wherein the RID peptide comprises the "epitope" portion as well as amino acids upstream and/or downstream of the "epitope" portion. Using the non-limiting AT1R example above, the full RID sequence may be ltsnqseyhfacvtintneiffvnrhi (SEQ ID NO:3), while the RID peptide may be snqseyhfacv (SEQ ID NO:19). The non-"epitope" portion of this embodiment of the RID peptide comprises one or more of the D-amino acids upstream of the "epitope" and/or one or more of the D-amino acids downstream of the "epitope."

In certain embodiments, the presently disclosed inventive concepts are directed to a peptide comprising a sequence of D-amino acids in a retro-inverso orientation based on a sequence comprising at least four consecutive residues of an L-amino acid sequence selected from the group consisting of SEQ ID NOs: 1 and 5-18, wherein the at least four residues may be any consecutive sequence within SEQ ID NOs: 1 and 5-18; in certain embodiments, the peptide comprises at least a portion of an epitope to which an autoantibody binds to the receptor comprising the specific SEQ ID sequence.

Peptide substitutions of the D-aa of the RID peptide may include D-amino acids individually and independently selected from groups comprising: (1) acidic amino acids; (2) basic amino acids; (3) individually and independently selected from the group comprising Leu, Ile, Val, Met, Trp, Tyr, and Phe; (4) individually and independently selected from the group comprising Ser, Thr, Ala, and Gly; (5) individually and independently selected from the group comprising Gln and Asn.

The RID peptides of the presently disclosed inventive concepts may be constructed to have a cyclic structure. A non-limiting example of a cyclic peptide is the following RID peptide:

(SEQ ID NO: 20)
cyclo-ltsnqseyhfacvtintneiffvnrhi.

In another embodiment, the RID peptides involve the use of multipin technology incorporating successive overlapping peptides (1-2 aa overlapping) of RID sequences. Use with polyclonal subject serum or derived IgG from same with ELISA techniques will permit identification of the specific target epitope (or multiple target epitopes) within the ECL of interest. This is illustrated by identification of the target epitope, for example but not by way of limitation, for B2AR ECL2; thus, this technology permits construction of a restricted RID peptide that may incorporate advantageous attributes. These attributes may include "personalized application" to a patients' autoantibody specificity.

The D-amino acid-containing peptides of the presently disclosed inventive concepts possess many advantages over the prior art, including but not limited to: (1) the ability to withstand all natural peptidases which can act on peptides comprising L-amino acids; (2) the capability for withstanding gastro-enteric exposure to natural peptidases and to limited acid hydrolysis; and (3) the potential for oral administration.

In another embodiment of the D-amino acid-containing peptides of the presently disclosed inventive concepts, the peptide is a mixed L-amino acid/D-amino acid peptide which comprises a binding epitope which is constructed of L-amino acids, while upstream and downstream portions of the peptide comprise one or more flanking D-amino acids on each end of the L-amino acid portion of the peptide; these flanking D-amino acids serve to protect the epitope containing natural L-amino acids that is located therebetween. For example, this embodiment of a D-amino acid-containing peptide constructed in accordance with the presently disclosed inventive concepts may have the structure:

xEPITOPEx, wherein "EPITOPE" represents the specific natural target L-amino acids, and x represents one or more D-amino acids for blocking peptidase activity. For example but not by way of limitation, x may be 1, 2, 3, 4, 5, 6, 7, 8, 9, 10, 11, 12, 13, 14, 15, 16, 17, 18, 19, 20, or more D-amino acids.

Non-limiting examples of mixed L-amino acid/D-amino acid peptides include the following (wherein the upper case letters indicate an epitope formed of L-amino acids, and wherein "x" is at least one D-amino acid):

|  | |
|---|---|
| xAFHYESQx | (SEQ ID NO: 21) |
| xHWYRATHQEx | (SEQ ID NO: 22) |
| xYWAFGRx | (SEQ ID NO: 23) |
| xAPEDETx. | (SEQ ID NO: 24) |

In particular embodiments, the length of each D-aa sequence (i.e., each "x" in the sequences above) can vary from 1 to 20, such as from 2 to 10. In one non-limiting embodiment, the peptide has two flanking D-amino acids. A specific non-limiting example of a mixed L-amino acid/D-amino acid peptide based upon the AT1R target peptide is as follows:

(SEQ ID NO: 25)
vcAFHYESQns.

The underlined upper case letters represent the natural L-amino acid, while the lower case letters represent substituted D-amino acids.

In certain embodiments, the presently disclosed inventive concepts are directed to a peptide comprising a sequence of L-amino acids based on a sequence comprising at least four consecutive residues of an L-amino acid sequence selected from the group consisting of SEQ ID NOs: 1 and 5-18, wherein the at least four residues may be any consecutive sequence within SEQ ID NOs: 1 and 5-18. The peptide also contains at least one D-amino acid flanking either end of the L-amino acid sequence of at least four consecutive residues of at least one of SEQ ID NOS:1 and 5-18. In certain embodiments, the L-amino acid portion of the peptide comprises at least a portion of an epitope to which an autoantibody binds to the receptor comprising the specific SEQ ID sequence.

The D-amino acid-containing peptide compositions of the presently disclosed inventive concepts may be administered in therapeutically effective amounts. An effective amount is a dosage of the composition sufficient to provide a therapeutically or medically desirable result or effect in the subject to which the composition is administered. The effective amount will vary with the particular condition being treated, the age and physical condition of the subject being treated, the severity of the condition, the duration of the treatment, the nature of the concurrent or combination therapy (if any), the specific route of administration, and like factors within the knowledge and expertise of the health practitioner. For example, in connection with methods directed towards treating subjects having a condition characterized by orthostatic hypotension, an effective amount would be an amount sufficient to mitigate, reduce, modulate, inhibit, or otherwise effectively treat the condition in the subject.

The compositions of the presently disclosed inventive concepts may further contain a conjugate of any of the D-amino acid-containing peptide compositions disclosed or otherwise contemplated herein associated with a labeling agent. Various methods of labeling peptides are known in the art and may be used in accordance with the presently disclosed inventive concepts. Examples of labels for polypeptides include, but are not limited to, the following: radioisotopes or radionuclides, fluorescent labels, chemiluminescent labels, and the like. In some embodiments, the labeling agent may be attached to the peptide by a spacer arm of various lengths to reduce potential steric hindrance. In addition, the terms "label", "labeling agent," "detectable marker," "detection moiety," and "reporter molecule" are used interchangeably herein. These conjugates are useful in various diagnostic methods, as discussed in more detail in the examples.

Generally, a therapeutically effective amount will vary with the subject's age, condition, and sex, as well as the nature and extent of the disease in the subject, all of which can be determined by one of ordinary skill in the art. The dosage may be adjusted by the individual physician or veterinarian, particularly in the event of any complication. A therapeutically effective amount is typically, but not limited to, an amount in a range from 0.1 µg/kg to about 2000 mg/kg, or from 1.0 µg/kg to about 1000 mg/kg, or from about 0.1 mg/kg to about 500 mg/kg, or from about 1.0 mg/kg to about 100 mg/kg, in one or more dose administrations daily, for one or more days. If desired, the effective daily dose of the active compound may be administered as two, three, four, five, six, or more sub-doses, for example, administered separately at appropriate intervals throughout the day, optionally, in unit dosage forms. In some embodiments, the inhibitors are administered for more than 7 days, more than 10 days, more than 14 days, or more than 20 days. In still other embodiments, the inhibitor is administered over a period of weeks or months. In still other embodiments, the inhibitor is delivered on alternate days. For example, the agent may be delivered every two days, or every three days, or every four days, or every five days, or every six days, or every week, or every month.

The compounds of the presently disclosed inventive concepts may be administered alone or in combination with the above-described drug therapies and may be administered by a variety of administration routes. The particular mode selected will depend, of course, upon the compound selected, the condition being treated, the severity of the condition, whether the treatment is therapeutic or prophylactic, and the dosage required for efficacy. The methods of the presently disclosed inventive concepts, generally speaking, may be practiced using any mode of administration that is medically acceptable, meaning any mode that produces effective levels of the active compounds without causing clinically unacceptable adverse effects. The administration may, for example, be oral, intraperitoneal, intra-cavity such as rectal or vaginal, transdermal, topical, nasal, inhalation, mucosal, interdermal, or parenteral routes. The term "parenteral" includes subcutaneous, intravenous, intramuscular, or infusion. Intravenous or intramuscular routes may not be particularly suitable for long term therapy and prophylaxis. In certain embodiments, however, it may be appropriate to administer the compound in a continuous infusion every several days, or once a week, or every several weeks, or once a month. Intravenous or intramuscular routes may be particularly used in emergency situations. Oral administration may be used for prophylactic treatment because of the convenience to the patient as well as the dosing schedule. Likewise, sustained release devices as described herein may be useful in certain embodiments for prophylactic or post-surgery treatment, for example.

Particular formulations of pharmaceutical compositions of the presently disclosed inventive concepts for parenteral administration include, but are not limited to, sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions, or suspensions, including saline and buffered media. Parenteral vehicles include, for example, sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating compounds, inert gases, and the like. The pharmaceutical compositions may conveniently be presented in unit dosage form and may be prepared by any of the methods well known in the art of pharmacy.

Compositions suitable for oral administration may comprise discrete units, such as capsules, tablets, and lozenges, each containing a predetermined amount of the inhibitor. Other compositions include suspensions in aqueous liquids or non-aqueous liquids such as syrup, an elixir, or an emulsion. In yet other embodiments, the particular vehicle is a biocompatible microparticle or implant that is suitable for implantation into the mammalian recipient.

Other embodiments of the presently disclosed inventive concepts include pharmaceutically acceptable compositions which comprise a therapeutically-effective amount of one or more of the compounds described herein, formulated together with one or more pharmaceutically acceptable carriers (additives) and/or diluents. As described in detail below, the pharmaceutically acceptable compositions may be specially formulated for administration in solid or liquid form, including, but not limited to, those adapted for the following: (1) oral administration, for example, aqueous or non-aqueous solutions or suspensions, tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a cream or foam; (5) sublingually; (6) ocularly; (7) transdermally; or (8) nasally.

Some examples of materials which can serve as pharmaceutically-acceptable carriers include, but are not limited to: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Formulations of the compositions of the presently disclosed inventive concepts suitable for oral administration may be, but are not limited to, in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), and/or as mouth washes and the like, each containing a predetermined amount of a compound of the presently disclosed inventive concepts as an active ingredient. A compound of the presently disclosed inventive concepts may also be administered as a bolus or paste.

In solid dosage forms of the compounds of the presently disclosed inventive concepts for oral administration (capsules, tablets, pills, powders, granules and the like), the compound or compounds may be mixed with one or more pharmaceutically-acceptable carriers, including, but not limited to, sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets, and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

Liquid dosage forms for oral administration of the compounds of the presently disclosed inventive concepts include, but are not limited to, pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents. Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

EXAMPLES

Examples are provided hereinbelow. However, the presently disclosed and claimed inventive concepts are to be understood to not be limited in its application to the specific experimentation, results and laboratory procedures. Rather, the Examples are simply provided as one of various embodiments and are meant to be exemplary, not exhaustive.

Example 1: Exemplary GPCR's on which D-Amino Acid-Containing Peptides can be Based There are various G-protein coupled receptors known to have autoantibodies that bind thereto, wherein said binding either activates or blocks the G-protein coupled receptor. The epitopes of the GPCR to which the autoantibodies bind can be used as models for designing autoantibody-blocking D-amino acid-containing peptides, in accordance with the presently disclosed inventive concepts. Non-limiting examples of these GPCRs are listed below, along with the physiologic symptoms typical of patients having autoantibody-related conditions specific for the receptor.

Angiotensin II Type 1 Receptor (AT1R):

Hypertension is observed in 20% of the population (60 million in the USA).

1. Primary aldosteronism is observed in 7-8% of the hypertensive population: 60% of this population has idiopathic adrenal hyperplasia (IAH), while the remaining 40% has aldosterone-producing adrenal adenoma (APA). The inventor and an Italian group have demonstrated elevated anti-AT1R receptor autoantibodies in most patients with an APA; the inventor has also demonstrated the autoantibodies in APA and in IAH. Approximately 70% are estimated using less sensitive ELISA. Sera from these subjects cause constriction of the cremaster artery assay, which is a prototypical "resistance" artery representative of those arteries known to contribute to increased blood pressure in mammals, and this can be blocked by a decoy peptide.

2. "Essential" hypertension without known etiology has not been completely screened, and the numbers are less than reported for primary aldosteronism; and in fact might include some of these subjects. However, these autoantibodies do not stimulate aldosterone production equally to native Ang II. They will suppress endogenous renin production, however, and thus these autoantibodies may still constitute a group of significant interest.

3. "Low renin essential hypertension"—It is estimated that up to 20% of the hypertensive population have this characteristic constellation of low renin and low nl aldosterone.

4. Preeclampsia is frequently associated with young mothers and first births. The prevalence is approximately 5-7.5% of pregnancies worldwide. Last year there were 6 million pregnancies in the USA alone. Three studies indicate that a large percentage of these patients with preeclampsia develop activating autoantibodies to the AT1R, and these autoantibodies are involved in the pathophysiology associated therewith. Blockade with an angiotensin receptor blocking (ARB) agent ends up blocking the receptor to both the autoantibody and to the native Ang II and compromises the placental-fetal blood flow, thus being a detrimental treatment option. Blockade of only the autoantibody would likely not lead to such compromise.

Alpha 1 Autonomic Receptor (α1AR):

Hypertension: A low percentage in one study was observed, but this study did not use sensitive testing. Another study demonstrated up to 40% of screened hypertensive subjects had such autoantibodies.

Postural Tachycardia Syndrome (POTS): Regarding the prevalence thereof, it is estimated that >500,000 patients are affected in the United States alone. It is frequently observed in teenage girls and to a lesser extent in older individuals. The inventor has reported that 14/14 subjects so studied with POTS have significant levels of α1AR and β1AR activating autoantibodies that appear to be causative of their disorder.

B2 Autonomic Receptor (β2AR) and Muscarinic M3 Receptor (M3R):

Idiopathic Orthostatic Hypotension: One in every 50 subjects is estimated to have some orthostasis (excessive drop of BP upon standing), and approximately ½ have an unknown (idiopathic) etiology. The inventor has demonstrated that a large number of these harbor autoantibodies to the β2AR and/or M3R. Those with associated β1AR tend to have a tachycardia at rest and those with associated M2R have a resting bradycardia. All tend to have decreased homeostatic autonomic responsiveness and demonstrate postural hypotension. Use of β-blockers tends to worsen the hypotension by blocking not only the autoantibodies incompletely but blocking the endogenous autonomic system as well.

Atrial tachyarrhythmias: The inventor has demonstrated that a very high number of subjects with Graves' hyperthyroidism and associated atrial fibrillation (AF) have 1 or more autoantibodies, including β1/2AR and M2R. These are known agonists that facilitate atrial fibrillation. AF is responsible for ⅓ of the strokes in the USA and a known associate of decreased cardiac function. There is evidence that 30% of Graves' subjects with AF fail to return to a normal sinus rhythm after correction of their hyperthyroidism. There is evidence that a portion of these may be maintained in AF by the co presence of these facilitatory autoantibodies. Since more than one autoantibody is implicated, targeted personalized medical suppression of the antibody without affecting the receptor appears to be a promising approach. It is established that orthosteric blockers for the βAR are only 60-80% effective when used for inhibition of the allosteric effects of the autoantibodies.

The inventor has also demonstrated in rabbit models that these autoantibodies have specific targeted effects on the atrial rhythm. β2AR facilitate development of sustained atrial tachycardias. β1AR autoantibodies facilitate development of Sinus and AV nodal tachyarrhythmias and in the presence of M2 activation facilitate AF. M2R autoantibodies with added muscarinic activation facilitate AF and ventricular tachyarrhythmias. The prevalence of these autoantibodies in AF associated with organic valvular and enlarged atria is not currently known, but we suspect up to 20% will have developed autoantibodies at some time in their course.

Idiopathic Dilative Cardiomopathy: This is probably the best characterized association of autoantibodies to a particular disorder. It is estimated that >50% of patients who have Idiopathic Dilative Cardiomyopathy harbor autoantibodies to the β1AR. Patients who have these autoantibodies have the worst prognosis for sudden cardiac death (SCD).

Post viral Myocarditis: Some subjects with Post viral Myocarditis develop autoantibodies and these may perpetuate the damage to the patient over a prolonged period (24). The presently disclosed peptides can be used to inactivate these autoantibodies.

Dopamine D1 (D1R) and D2 (D2R) Receptors:

A significant number of children with Pediatric Autoimmune Neuropsychiatric Disorders Associated with Streptococcal infections (PANDA) have obsessive-compulsive ideation, motion and/or development disorders. A significant number of these subjects harbor autonomic antibodies to the Dopamine D1 and D2 receptors. These autoantibodies are stimulatory and inhibitory to several important functions in the brain by activation of their respective receptors. An example is Sydenham's chorea which is a consequence of autoantibodies to the dopamine D2R/D1R associated with a post streptococcal infection. The availability of a decoy that could be absorbed orally or given intravenously and would cross the blood brain barrier would have great potential value.

Alpha2A Autonomic Receptors (α2AR):

Raynauds' syndrome is a frequent autoimmune condition associated with temperature sensitive focal and systemic increased vasoactivity that is painful and leads to ulceration of digits and vascular insufficiency. It is frequently concomitant with other autoimmune diseases. Activation of the α2AR has been demonstrated to lead to the vasoconstriction. We are developing a RID to block these autoantibodies activating this receptor to determine if this will be a therapeutically useful approach.

Thyroid Stimulating Hormone (TSH) Receptor:

This is the most prevalent type of hyperthyroidism and 90-95% of the patients demonstrate elevated autoantibodies that activate the TSH receptor. If the antibody target(s) on the N terminus (alpha subunit) is/are identified, then specific medical therapy would be possible using the RID decoy technology.

Example 2: Background and Significance of Targeting AutoAntibodies Against Cardiac GPCR's Autoantibodies in Graves' Hyperthyroidism:

B1/2AR and M2R activation "trigger" atrial ectopy and facilitate induction and maintenance of a "substrate" for AF. Autoantibodies (AAb) against BAR and M2R in cardiomyopathies and atrial arrhythmias were identified in the last 20 years. A markedly increased prevalence of AAb to BAR and M2R has been demonstrated in subjects with Graves' disease with AF. These observations are significant since the concurrence of excess thyroid hormone, age, activation of BAR and M2R, and underlying cardiac disease facilitate development of atrial tachyarrhythmias. Furthermore, therapeutic reduction of thyroid hormone concentration alone does not lead to return of normal sinus rhythm in 30% of these patients, suggesting persistence of the AAb may be factorial.

Atrial Tachyarrhythmias:

Although sinus and atrial tachycardias are more common rhythm disturbances with thyrotoxicosis, AF is most important because of higher morbidity. The prevalence of AF in hyperthyroidism increases in stepwise fashion to greater than 20% in patients older than 70. The causation of AF in hyperthyroidism is incompletely understood and until recently has been attributed solely to excess thyroid hormone, an aging heart and/or underlying disease. There is general awareness this is an oversimplification.

It is convenient to consider 1) "triggering" (or initiating events) such as premature atrial contractions (PAC) or atrial tachycardia and 2) "substrate" considerations that contribute to the likelihood the ectopic beat encounters some conduction block, spatial dispersion, and development and sustenance of abnormal circular rhythms. These changes are often related as "remodeling." It has been demonstrated that conditions that increase or prolong the Ca' transient in the presence of an abbreviated action potential duration (APD) lead to early after depolarizations (EADs) and trigger arrhythmia through alterations in Na—Ca exchange. BAR and M2R activation from any source would lead to a similar outcome.

Effect of Autoantibodies on GPCR Function:

This complex topic is summarized in several reviews. Orthosteric ligands generally work within the internal pocket formed by the unique structure of the G-protein coupled receptors (GPCR) and rely on multiple interactions based on the structural requirements of the ligand and receptor. Less is known about the interactions of AAb, but their size, specificity and function targeted toward the 2nd>1st and variably the 3rd extracellular loop (ECL) support an allosteric function. Bornholz et al. have summarized evidence demonstrating β1AR autoantibody activation produces an allosteric impact on isoproterenol-induced orthosteric activation/inhibition. Their studies using a FRET labeled β1AR demonstrated a variable impact of the autoantibodies on isoproterenol stimulation of cAMP. They found some correlation of cAMP production with the ability of the autoantibody to inhibit concurrent internalization of the β1AR. This effect, however, was not universal and raises the question whether the internalization was directly related to autoantibody effectiveness or was an epiphenomenon. Data obtained by the inventor suggests an enhancement of both β1AR and β2AR agonist effects of isoproterenol by patient and rabbit derived β1AR and β2AR AAb. There are no data demonstrating primarily blocking antibodies to β1/2AR and M2R. However the inventor has identified at least 3 AAb possessing activating capacity when the orthosteric ligand is absent but with significant partial agonist effects when their respective orthosteric ligand is present. Additional issues are raised since GPCR may act in a heterogenic fashion. Antibody binding may well alter this interaction and either impede or facilitate receptor function under certain circumstances.

βAR Activity in Cardiomyocytes:

βAR activation increases cAMP, activates L-type Ca channels, and increases the movement of $[Ca^{2+}]_e$ to $[Ca^{2+}]_i$. Increased cytosolic $Ca^{2+}$ enhances a repolarizing transient outward $K^+$ current, which accelerates repolarization in myocytes. BAR/cAMP-mediated phosphorylation enhances the repolarizing $K^+$ current, accelerating repolarization and shortening refractoriness, and promoting both triggered firing and reentry. β1/2AR/cAMP-mediated phosphorylation of phospholamban enhances $Ca^{2+}$ uptake and overloading in the sarcoplasmic reticulum (SR), which in turn promotes spontaneous release of SR $Ca^{2+}$ and generation of delayed (DAD) and early (EAD) after depolarizations and resultant triggered firing. An inward (depolarizing) current, $I_f$, flowing in diastole, is augmented by phosphorylation mediated by cAMP, accelerating diastolic depolarization, and promoting automatic firing in specialized fibers in the atria. The IKs current is also sensitive to adrenergic stimulation but may not be so important in the atrial sleeve myocardium. Thus, sustained βAR activation results in increased automaticity, contractility, and circumstances favoring development of atrial tachyarrhythmias. This alteration in $Ca^{2+}$ homeostasis enhances automatic firing in specialized conducting cells, facilitates conduction (including the Purkinje system) and reduces the refractory period of the AV node. This electrical remodeling appears to be a major determinant of atrial tachyarrhythmia and AF induction and its measurement is an important parameter of AAb activity.

Cholinergic Effects on Atrial Function:

Muscarinic agonists, acting primarily through M2R, inhibit automaticity in the SA node, slow conduction and prolong the refractory period of the AV node and Purkinje fibers, and exert negative inotropic effects on atrial and ventricular myocytes. M2R agonists activate abundant $I_{KACH}$ channels in the atrium as well as the atrial sleeves extending into the pulmonary vein apertures. This is associated with a significant reduction in the APD and the effective refractory period (ERP) in atrial cells and increases the substrate for BAR-mediated triggering of EAD formation and re-entry. Acute administration of increasing dosages of the M2 agonist acetylcholine paradoxically will activate sympathetic neurons via the cardiac ganglia and induce atrial tachyarrhythmias and AF in the presence of a susceptible substrate.

The importance of the autonomic nervous system (ANS) for initiation and maintenance of AF is supported by emerging evidence from both basic and clinical studies. ANS activation facilitates EAD and triggered activity by simultaneously prolonging the intracellular calcium transient (sympathetic effect) and shortening the APD (parasympathetic effect), suggesting a synergistic effect between sympathetic and parasympathetic activation on atrial arrhythmogenesis. Sharifov et al. infused isoproterenol and acetylcholine into the canine sinus node artery and found the β-agonist isoproterenol increased the likelihood and ease of AF induction with acetylcholine compared with acetylcholine alone. Similarly, Patterson et al. showed that simultaneous injections of acetylcholine and norepinephrine into canine pulmonary vein ganglions led to pause-dependent induction of triggered activity and arrhythmias arising from the pulmonary veins. These data support the concept that combined sympathovagal activation is profibrillatory.

Thyroid Hormone on Atrial Function:

Tri-iodothyronine (T3) has an impact on cardiac function. This active thyroid hormone increases phospholamban phosphorylation similar to but not identical to that of BAR agonists. This increases activity of the $Ca^{2+}$-ATPase regulating SR $Ca^{2+}$ storage and shortens the APD, increases contractility, and increases the likelihood for development of DAD when SR overloading occurs. These effects appear to include alteration of the functional properties of the Na channel and the $I_k$ currents. The net result of increased thyroid activity is an increase in atrial automaticity, shortening of the APD and refractory period, and an increased likelihood for development of afterdepolarizations. The inventor has demonstrated that these effects are additive to those for BAR and M2R.

Graves' hyperthyroidism exhibits signs of adrenergic overactivity, including tachycardia, glucose intolerance, excess energy utilization, and autonomic instability. Circulating catecholamines, however, are generally suppressed, and several autonomic functions demonstrate increased sensitivity to β blockade. This has led to the concept of an increased sensitivity of the βAR to compensate for the decreased circulating catecholamines. However, experimental induction of hyperthyroidism using exogenous thyroid in an animal model does not reproduce BAR hypersensitivity. The present disclosure is the first to report increased autonomic sensitivity to AAb with excess thyroid hormone (see Example 4).

The Effect of Age on AF:

Overt hyperthyroidism and aging are associated with AF; the reported prevalence being 5% to 20% and higher with increasing age. The mechanisms for this propensity for AF in aged individuals are not clear. Atrial fibrosis and stretch increase with age and stress of cardiac diseases and certainly may be a factor in hyperthyroidism and AF since aging is an important co-factor. Evidence also supports the concept that age reduces extrinsic control of intrinsic cardiac ANS activity allowing focal firing from adjacent pulmonary vein (PV) atrial tissue and predisposes the elderly to AF. The prevalence of autoimmune disorders is bipolar for the young and aging; and is associated with such changes as might occur with generation and activity of the AAb.

Based on historical and the inventor's own data, FIG. 1 represents a current formulation to explain the pathophysiology of AF in hyperthyroid states. This demonstrates the association of excess thyroid hormone, increased age, and AAb with the adrenergic and muscarinic receptors in initiation and maintenance of the AF. This figure is used for the specific circumstances associated with hyperthyroidism and is not exclusive of the pro-arrhythmic effect of these same AAb in other forms of cardiac arrhythmias.

Example 3: AT1R-ECL2—RID Peptide

The coexistence of agonistic autoantibodies to β1 and β2 adrenergic receptors (β1/2AR) and muscarinic M2 and M3 receptors (M2/3R) has been identified in a number of patients with orthostatic hypotension (OH). These autoantibodies also may act as an etiologic or functional component of cardiomyopathy, myocarditis, and cardiac arrhythmias. Activating autoantibodies to the angiotensin II receptor (AT1R) and the α1 adrenergic receptor (α1AR) have also been identified as likely etiological agents in hypertensive disorders and in postural tachycardia syndrome (POTS). These autoantibodies occasionally are observed in the sera of healthy subjects, but generally in a lower frequency and in lower titers. Among the effects these functionally active antibodies are predicted to have in patients are: (a) β1/2AR activation-induced resting tachycardia and β2AR-mediated peripheral vasodilatation, (b) β1/2AR induced or associated myocardopathy, (c) M2R activation-induced resting bradycardia and inhibition of heart rate increase despite peripheral vasodilatation, and a decreased ventricular contractility despite adrenergic stimulation, (d) M3R activation-induced vasodilatation via endothelial nitric oxide synthase (eNOS) activation, (e) α1AR partial antagonism leading to POTS, and/or (f) AT1R induced hypertension, and (g) pre-eclampsia related fetal and maternal risks.

A balance between these coexisting and sometimes opposing autoantibodies likely accounts for a broad range of expression in these subjects with variable heart rate, degrees of vasodilatation, and cardiac dysfunction. These autoantibodies, by their very nature, will induce predictable hemodynamic changes. Although the autoantibody effects may not be sudden, their presence will compromise appropriate compensatory cardiovascular responses to upright posture in OH patients for example. It has also been discovered that autoantibodies to α1AR and AT1R are also operative in hypertensive patients, in those with refractory hypertension ("Potential relevance of alpha 1."; PLoS ONE, November 2008, e 3742-), and also in those with primary hyperaldosteronism (PA).

The large number of disease states related to the presence of these activating autoantibodies and lack of specific therapies for their treatment is a significant problem for medical research, pharmacological research and development, and patient management.

Several assays have been developed to demonstrate the presence of these autoantibodies and to measure the wide variety of biological and physiological responses related to their presence in human disease and animal models of the human diseases. These include ELISA, activation of specific receptor-transfected cells, and vasoconstriction/vasodilatation of isolated perfused cremaster arteries. These assays permit the examination of the presence and activity of these autoantibodies in vitro as well as while circulating in animal models of human disease.

The target peptides have been identified for several of these receptor complexes. When a rabbit is immunized with this peptide, antibodies that function identically to that observed in the human can be reliably produced. The inventor and others have demonstrated these autoantibodies can be blocked with the targeted L-amino acid-based peptide.

Normal peptide structure in living cells and tissues is based entirely on L-amino acids. Peptidases in humans fail to act on peptide structures based on D-amino acids. The presently disclosed inventive concepts are directed to target peptides which (1) comprise only D-amino acids (or a combination of D- and L-amino acids) for blocking action of (a) dipeptidases from either end after infusion into the living organism and (b) endopeptidases attacking selective amino acid structures. While this substitution of L-amino acids with D-amino acids protects the peptide from degradation in the body, the structure and orientation of the accessory side chains is changed, thereby altering the interaction of the novel peptides with the autoantibodies targeting that epitope. In the present novel peptides therefore, to preserve this interaction, the molecular sequence of the respective amino acids in the peptide has been inverted, and (2) the amino-carboxyl linkage sequence has been reversed.

As shown in FIG. 2, the epitope of the second extracellular loop (ECL) of the AT1R receptor has been used as the basis of a retro-inverso D-amino acid ("RID") peptide according to the presently disclosed inventive concepts. The second ECL2 has the sequence: IHRNVFFIENTNITVC AFHYESQNSTL (SEQ ID NO:1), wherein the autoantibody binding epitope is underlined, and has the sequence AFHYESQ (SEQ ID NO:2), which is the primary target for the autoantibodies to ECL2. The retro-inverso D-amino acid version of ECL2 has the sequence: ltsn qseyhfacvtintneiffvnrhi (SEQ ID NO: 3), wherein the D-amino acids are represented in lower case, and wherein the retro-inverso D-amino acid version of the binding epitope sequence is underlined and has the sequence: qseyhfa (SEQ ID NO: 4).

This format, called "retro-inverso-D" (RID), is shown in FIG. 2 to create a "mirror image" of the original peptide comprised of L-amino acids and has the unique feature that the reverse side of this peptide places all of the accessory side chains into the identical orientation as in the original L-amino acid peptide. This side consequently is available for interaction with the autoantibodies and is capable of binding it; but with the conferred protection against proteolysis that is not shared by the L-amino acid peptide. This peptide therefore serves as a "decoy" and inhibits the autoantibody from binding to its cell membrane bound receptor, thereby inhibiting the agonistic or antagonistic activity of the autoantibody. This effect thus decreases the activity of the autoantibody, and leading to clearance of the decoy peptide-autoantibody complex by known clearance mechanisms. Potentially this will lead to the body developing "tolerance" to this epitope and suppression of autoantibody production.

Data provided herein were obtained with immunized rabbit serum containing autoantibodies that will stimulate AT1R receptors transfected into CHO cells. These antibodies were equally blocked in sera taken from immunized rabbits that were injected with either the L-amino acid peptide or the RID peptide (Panels A-B of FIG. 3). These data demonstrate that the affinity of the autoantibodies to the longer lasting RID (D-amino acid) peptide of the presently disclosed inventive concepts is equivalent to the short-lived natural (L-amino acid) target. A bioassay for Angiotensin II-like activity using an isolated perfused cremaster artery in vitro has also been developed. FIG. 4, Panel A uses this assay to demonstrate the contractile effect of the serum from an immunized rabbit model. FIG. 4, Panel B demonstrates the impaired effect of the serum taken from a rabbit treated with the RID peptide compared to its control. The short-lived natural L-amino acid peptide showed a similar inhibitory effect 90 minutes after its infusion. FIG. 5, Panels A-B demonstrate the effect of adding either the natural L-amino acid peptide or the RID (D-amino acid) peptide to serum in vitro for 2 hours on inhibition of the autoantibody-induced contractility in the cremaster artery.

TABLE 2

Effect of AT1R-ECL2 RID Peptide on Induced Atrial Tachyarrhythmias in AT1R-Immunized Young Rabbits

| Atrial Tachyarrhythmias | Pre-Immune | Post-Immune | Post-Immune + RID (30 min) | Post-Immune + RID (90 min) |
|---|---|---|---|---|
| Sustained | 0/12 | 7/12 | 0/10 | 1/12 |
| Non-sustained | 4/12 | 11/12 | 10/10 | 1/12 |

Table 2 demonstrates the effect of activating autoantibodies in immunized rabbits (n=3) on atrial tachyarrhythmias. The rabbits were anesthetized and a co-axial catheter is inserted via the jugular vein into the heart with the stimulus electrode in the atria sinus region. The ECG was recorded before and after stimulation with acetylcholine and brief rapid atrial stimulation (burst pacing). Induction of transient and sustained atrial tachyarrhythmias was measured during the pre-immune state and 6 weeks after immunization with the L-amino acid target AT1R 2nd ECL peptide. The average AT1R autoantibody titer was >1:1.25 million at this point (in vitro activity data are shown in FIGS. 3, 4, and 5). The RID peptide (2 mg/Kg BW IV) was then infused over 5 minutes, and the animals' hearts were re-stimulated after 30 minutes and 90 minutes. There was a significant increase in both sustained and non-sustained tachyarrhythmias in the post immune animals. These included sinus, junctional, and atrial tachycardias. There was a marked decrease in sustained events at 30 and 90 minutes after RID infusion. The decrease in transient events was not observed at 30 minutes but was highly significant at 90 minutes.

Table 2 demonstrates the impact of autoimmunization that leads to activation of the AT1R receptor on atrial tachyarrhythmias. There is a dramatic increase in sustained and non-sustained (transient) atrial events following atrial stimulation in the immunized animals compared to their pre-immune state. Thirty and ninety minutes after infusion of the RID peptide, there was an almost complete suppression of the sustained events and a dramatic decrease in the non-sustained (transient) events.

In FIG. 6, nine rabbits were immunized with a multiple antigen peptide (MAP) containing the known AT1R-AAb epitope (AFHYESQ, SEQ ID NO:2) to induce hypertension therein. Then the impact of 0.5% Na and lo Na intakes, along with the RID AT1R-ECL2 decoy peptide, on AAb activity were examined. The RID peptide administered IV rapidly lowered the Systolic and Diastolic BP levels back to normal.

In addition, these animals were examined for changes in their atrial stimulation threshold using the identical protocol; an increased sensitivity to the burst pacing and Ach was demonstrated, along with a marked increase in non-sustained and sustained atrial tachyarrhythmias including AF. However, these tachyarrhythmias were abolished within 90 minutes of IV administration of the AT1R-ECL2-RID peptide.

These data support the use of a decoy peptide that is effective in a specific fashion for this AT1R receptor, in accordance with the presently disclosed inventive concepts. These data serve as a model for RID technology applied specifically to other GPCR-autoantibody interactions, and in general to all other autoantibody-specific target epitope interactions.

Example 4: β1AR-ECL2—RID Peptide

Example 3 demonstrated that the AT1R-ECL2 RID decoy peptide rapidly and effectively blocks the hypertensive effects of AT1R-AAb in the rabbit model. Moreover, the AT1R-ECL2 RID peptide virtually eliminated the induction of sustained and non-sustained atrial tachyarrhythmias in the same model without apparent sequelae. In this Example, a similarly dramatic effect of the β1AR-ECL2 RID decoy peptide was observed.

As shown in FIG. 7, the epitope of the second extracellular loop (ECL) of the β1AR receptor was used as the basis of a retro-inverso D-amino acid ("RID") peptide according to the presently disclosed inventive concepts. The top peptide structure is of the β1AR ECL2 L-amino acid epitope (RCYNDPKCCD; SEQ ID NO:2) that is the target for activating autoantibodies. The retro-inverso D-amino acid (RID) peptide (dcckpdnycr; SEQ ID NO:27) that has been constructed in accordance with the presently disclosed inventive concepts is shown in the bottom peptide structure, and the RID peptide is based on the native L-amino acid sequence shown in the top peptide structure. The RID peptide serves as a "decoy" target for the activating autoantibodies against β1AR.

Figure 9:
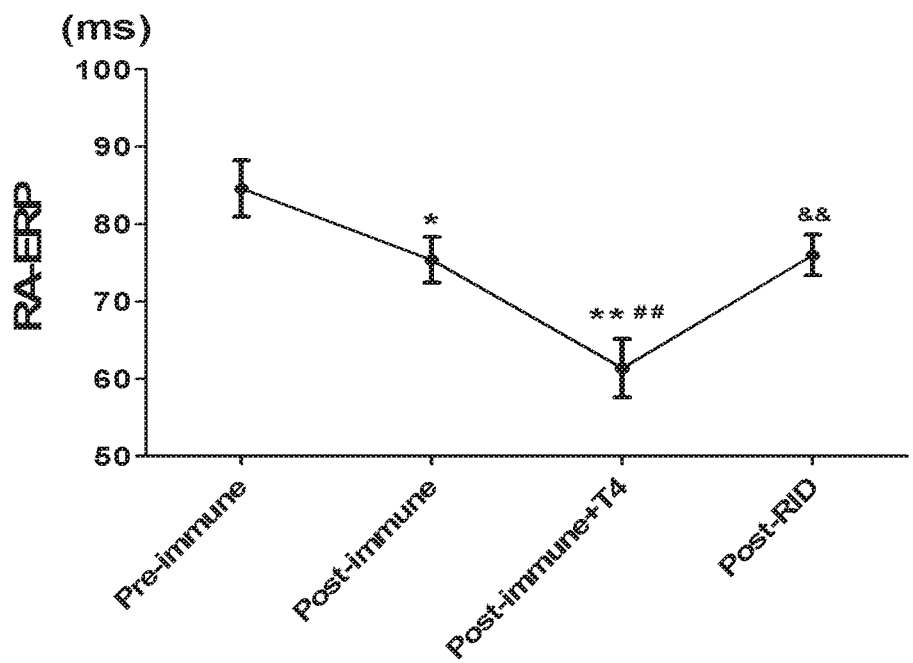
FIG. 9 graphically illustrates the effects of β1AR-ECL2 RID peptide and thyroxine (T4) on ERP in β1AR-immunized rabbits. *$P<0.05$, **$P<0.01$ vs. pre-immune; #$P<0.05$, ##$P<0.01$ vs. post-immune; &$P<0.05$, &&$P<0.01$ vs. post-immune+T4.

The RID peptide was utilized in a study measuring the effective refractory period (ERP) in five New Zealand white rabbits. The procedures performed are outlined in the flow chart of FIG. 8. The ERP was measured during a pre-immune state and following immunization with β1AR ECL2 peptide to generate autoantibodies thereto, as described previously (Li et al. *Am J Physiol Heart Circ Physiol*. (2014) 306:H422-428). This was followed by administration of T4 (40 µg/kg), and an additive effect was observed on induced atrial tachyarrhythmias with the appearance of AF in a significant percentage of the T4 treated animals. Of particular note was the impact of each treatment on the ERP (as shown in FIG. 9). These data confirm the additive changes in electrical modeling induced by β1AR-AAb and T4 treatment. In addition, the ERP in the rabbits was measured following administration of the β1AR-ECL2 RID peptide 90 minutes after T4. As shown in FIG. 9, β1AR immunization caused a significant decrease in the ERP (P<0.05), and T4 effects were additive (P<0.01). However, blockade of the β1AR-AAb with RID reversed the β1AR-AAb effects but not the effect caused by T4.

Figure 10:
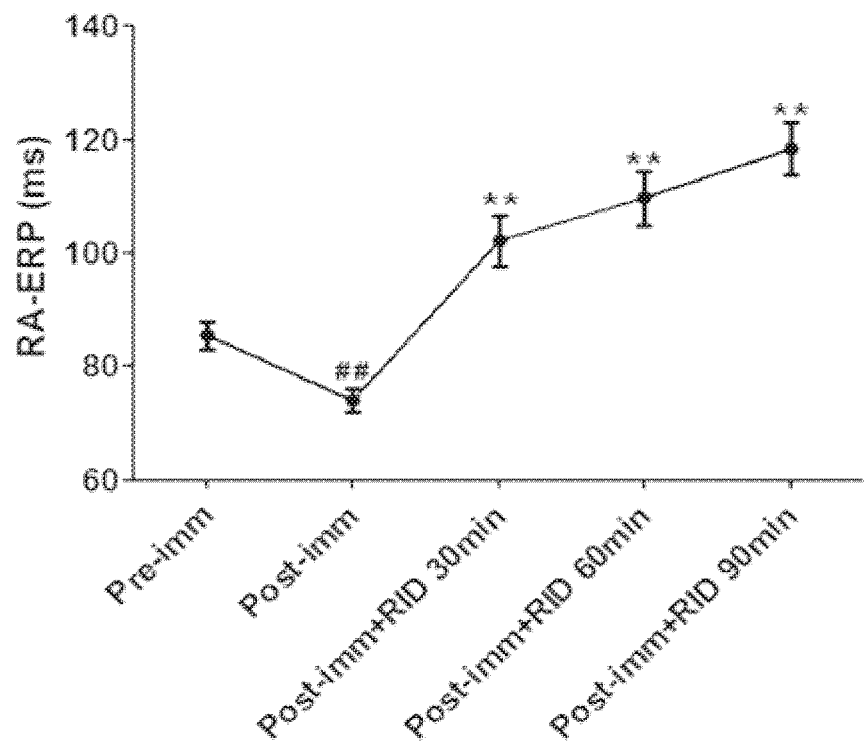
FIG. 10 graphically illustrates that β1AR-ECL2 RID peptide reverses the shortening of the ERP (in msec) observed in β1AR-immunized rabbits who harbor the β1AR-AAb. ##$P<0.01$ Compared with pre-immune; **$P<0.01$ compared with post-immune using paired t test. ERP, effective refractory period; RA, right atrial.

FIG. 10 illustrates the mean ERP for an atrial catheter lead. The ERP dropped significantly (p<0.01) following β1AR-ECL2 immunization over six weeks. However, IV administration of the β1AR-ECL2 RID peptide caused a dramatic rise in ERP over a 90 minute period.

Figure 11:
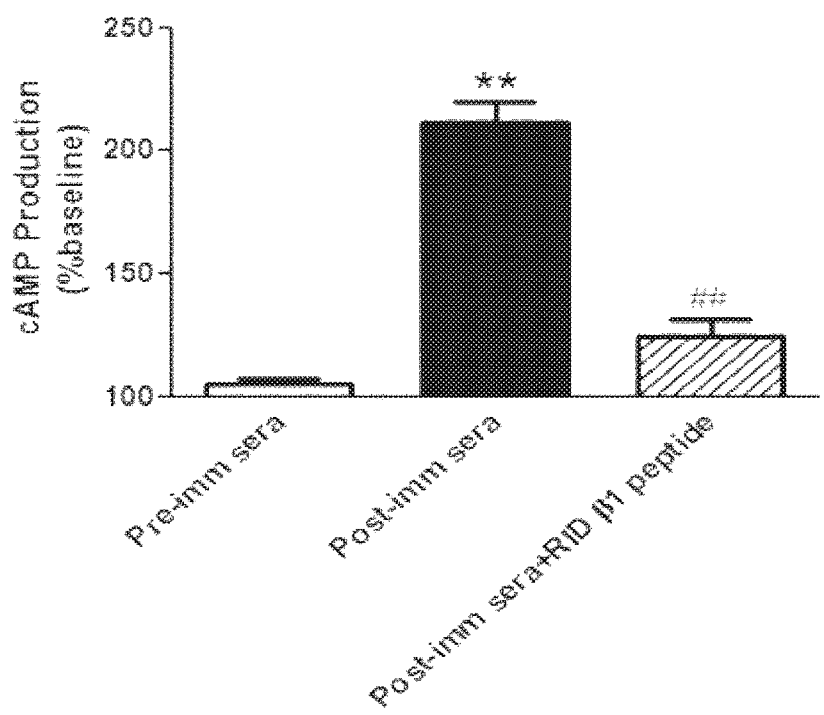
FIG. 11 shows post-immune rabbit sera containing β1AR-AAb stimulated cAMP production in β1AR-CHO cells. Sera taken from the same rabbits 90 after IV injection of the β1AR-ECL2 RID peptide (1 mg/Kg BW) demonstrated marked reduction of the ability to stimulate cAMP.

FIG. 11 demonstrates the effect of the β1AR-ECL2 RID peptide on immunized rat sera on cAMP production in β1AR-transfected cells in vitro. Compared to the pre-immune sera, the anti-β1AR sera significantly increased cAMP production (**P<0.01), while pre-incubation with the RID peptide for β1AR effectively blocked the sera-induced β1AR activation of cAMP production (##β<0.01).

TABLE 3

Effect of β1AR-ECL2-RID Peptide on HR and Sustained Atrial Arrhythmias in β1AR-AAb + T4 Excess Animals.

| EP response | Pre-immune | Post-immune | Post-immune + T4 | Post-immune + T4 + β1AR-RID |
|---|---|---|---|---|
| Heart rate (beats/min) | 188 ± 30 | 20 ± 31 | 280 ± 56**## | 241 ± 35**##+ |
| #sustained arrhythmias/ #induction attempts | 0/20 | 13/20** | 20/20**# | 6/20*++ |
| Sustained ST | 0/20 | 9/20* | 11/20** | 3/20+ |
| Sustained JT | 0/20 | 2/20 | 2/20 | 2/20 |
| Sustained AT | 0/20 | 1/20 | 2/20 | 1/20 |
| Sustained VT | 0/20 | 0/20 | 3/20 | 0/20 |
| Sustained AF | 0/20 | 0/20 | 2/20 | 0/20 |
| Sustained AFL | 0/20 | 1/20 | 0/20 | 0/20 |

AFL, atrial flutter; AF, atrial fibrillation; AT, atrial tachycardia; JT, junctional tachycardia; ST, sinus tachycardia; VT, ventricular tachycardia. *P <0.05, **P <0.001 vs. pre-immune; #P <0.05, ##P <0.001 vs. post-immune; +P <0.05, ++P <0.001 vs. post-immune + T4.

This Example demonstrates the powerful decoy effects of RID technology on atrial tachyarrhythmias induced and spontaneously occurring in β1AR-ECL2 immunized rabbits.

Example 5: B2AR-ECL2—RID Peptide

As shown in FIG. 15, the epitope of the second extracellular loop (ECL) of the B2AR receptor was used as the basis of a retro-inverso D-amino acid ("RID") peptide according to the presently disclosed inventive concepts. The top peptide structure is of the β2AR ECL2 L-amino acid epitope (HWYRAT; SEQ ID NO:28) that is the target for activating autoantibodies. The bottom peptide structure is of the retro-inverso D-amino acid (RID) peptide (tarywh; SEQ ID NO:29) that has been constructed in accordance with the presently disclosed inventive concepts and is based on the native L-amino acid sequence shown in the top peptide structure. The RID peptide serves as a "decoy" target for the activating autoantibodies.

Example 6: Stability, Immunogenicity, and Further Utility of the RID Peptides

FIGS. 12 and 13 demonstrate a stability/metabolism study of the AT1R-ECL2 RID peptide. In FIG. 12, the AT1R-ECL2 L-amino acid peptide and the AT1R-ECL2 RID peptide were each separately incubated in normal human serum at 37° C., and proteolysis of the peptides was measured by HPLC. As can be seen in FIG. 12, rapid proteolysis of the AT1R-ECL2 L-amino acid peptide was observed, with complete loss of integrity by 45 minutes. In contrast, the AT2R-ECL2 RID peptide remained intact at two hours, and 80% was observed to still be intact at 24 hours (data not shown).

In FIG. 13, the AT1R-ECL2 L-amino acid peptide and the AT1R-ECL2 RID peptide were each separately incubated in artificial gastric juice (SGF, pepsin+HCL, pH 1.2) at 37° C., and proteolysis of the peptides was measured by HPLC. The AT1R-ECL2 RID peptide remained intact in the gastric fluid for four hours, and 60% was observed to be remaining at six hours. As expected, the AT1R-ECL2 L-amino acid peptide was more stable in the artificial gastric juice compared to the normal human serum; however, as can be seen in FIG. 13, the native peptide was proteolyzed at a much faster rate than the RID peptide.

In addition, the immunogenicity of the RID peptides has also been briefly studied. A rabbit was immunized with the β1AR-ECL2 RID peptide but failed to demonstrate anti-RID antibodies, as measured by ELISA (data not shown). This data demonstrates that the RID peptides are also non-immunogenic.

While therapeutic methods of using the RID peptides have been envisioned above, the scope of the presently disclosed inventive concepts also includes diagnostic uses of the RID peptides as well. The studies shown in FIGS. 12 and 13 were conducted at high concentrations (>250 μg/ml), and these concentrations are too high for study of absorption and use as part of a direct assay of serum binding to autoantibodies. The AT1R-ECL2 RID peptide has been iodinated successfully, but the presence of the iodine atom in this molecular structure blocked binding.

Figure 14:
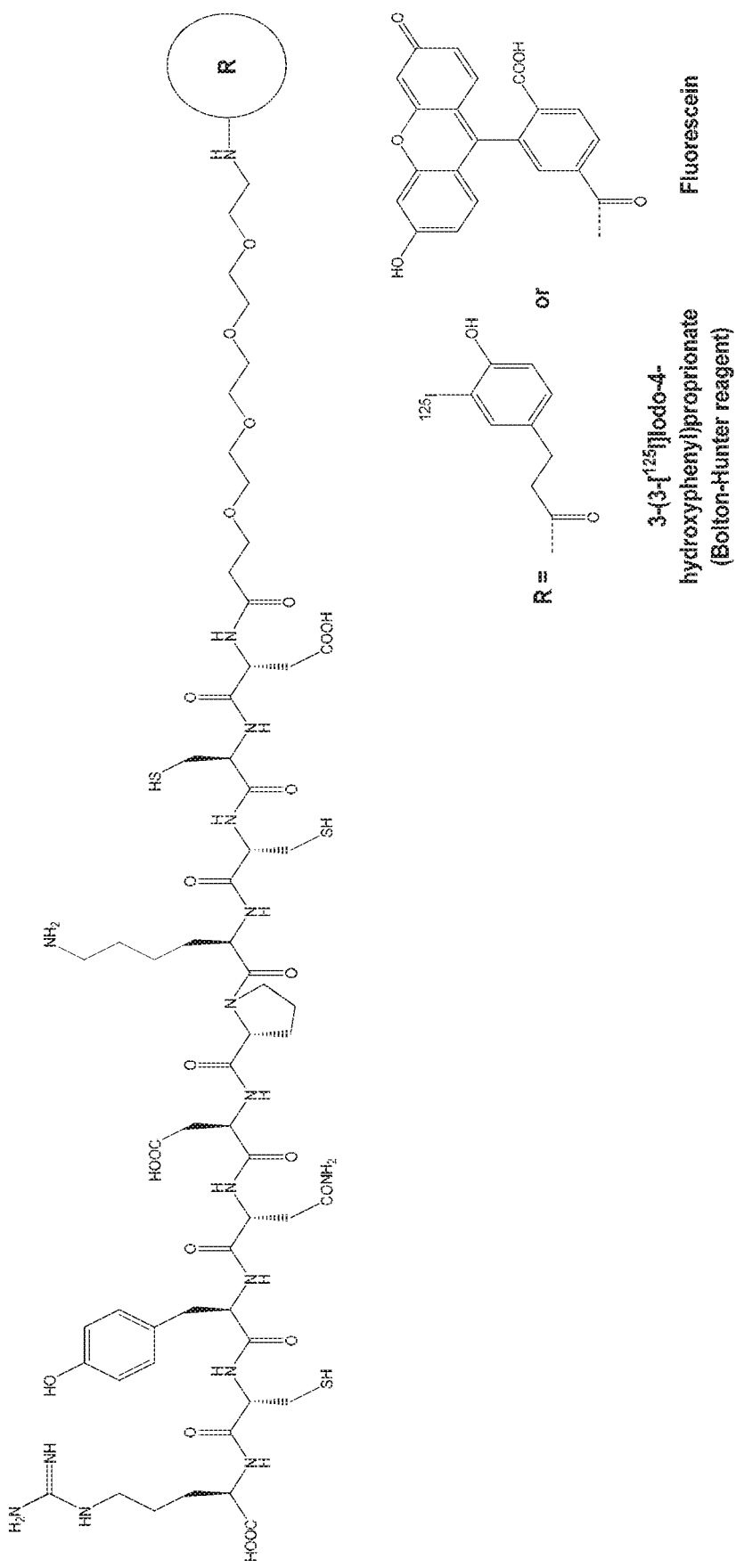
FIG. 14 contains the structures of an AT1R-ECL2 RID conjugate synthesized by inserting a PEG4 spacer in between the AT1R-ECL2 RID peptide and either a fluorescein molecule or a 3-(3-[$^{125}$I]Iodo-4-hydroxyphenyl)propionate (Bolton-Hunter reagent) molecule. This construction permits insertion of reporter molecule(s) such as an isotope of fluorescein without interfering with peptide secondary structure-AAb interactions.

Thus, a new AT1R-RID, β1AR-RID, or generalized GPCR-ECL2-RID conjugate is synthesized in which a PEG4 spacer is inserted in between the peptide and either a fluorescein molecule or a 3-(3-[$^{125}$I]Iodo-4-hydroxyphenyl) proprionate (Bolton-Hunter reagent) molecule that will not interfere with AAb binding (see FIG. 14). The use of Bolton-Hunter reagent for radioiodination eliminates the possibility of iodinating the intrinsic tyrosine, which appears to be essential for the antibody binding. This is an indirect radioiodination method in which an acylating reagent, N-succinimidyl-3-(4-hydroxyphenyl)proprionate, is first radioiodinated to obtain N-succinimidyl-3-(3-[$^{125}$I]Iodo-4-hydroxyphenyl)proprionate and purified on the HPLC. The purified N-succinimidyl-3-(3-[$^{125}$I]Iodo-4-hydroxyphenyl) proprionate is then covalently coupled to the free —NH2 group present on the peptide. This provides two alternative probes.

Synthesis of β1AR ECL2 RID peptide with attached fluorescein or tyrosine begins with synthesis of B1AR-RID-PEG4 by the solid phase peptide synthesis method manually in 0.05 mmole scale using our previously reported conditions (Pathuri et al. *Bioconjug Chem*, 23:115-124, 2012). Then, commercially available N-hydroxysuccinimide (NHS)-Fluorescein is utilized for synthesizing β1AR-RID-PEG4-Fluorescein. NHS esters reacts efficiently with the free primary amino group (—NH2) of β1AR-RID-PEG4 in pH 7-9 buffers to form a stable amide bond. Radioiodination (iodine-125 or 123) will be carried out using commercially available water-soluble Bolton-Hunter reagent (*Biochem J* 133:529-539, 1973). The peptides are purified by HPLC.

The iodinated RID peptides can be used in various imaging methods (including but not limited to, SPECT/CT systems). This permits examination of the distribution of the RID-$^{123}$I in various organs, such as but not limited to, brain, heart, kidney, and muscle, as well as the examination of levels in urinary excretion. The fluorescein tagged RID peptides can be used for non-radioactive fluorescence quantification in similar assays. Both iodinated and fluorescein-labelled peptides will be successful for both assays of sera for RID-peptide specific AAb, and these assays will provide proportionate binding and receptor activity. They will also demonstrate gastric absorption, tissue distribution, and access to the CNS. The primary route in non-immune animals will be via the kidney while hepatic/splenic clearance for those with immune complexes. These data can thus be used in preparing these compounds for future clinical applications.

Although the presently disclosed inventive concepts and the advantages thereof have been described in detail, it should be understood that various changes, substitutions and alterations can be made herein without departing from the spirit and scope of the presently disclosed inventive concepts as defined in the present disclosure. Moreover, the scope of the present application is not intended to be limited to the particular embodiments of the processes, compositions of matter, means, methods and steps described in the specification. As one of ordinary skill in the art will readily appreciate from the disclosure of the presently disclosed inventive concepts, processes, compositions of matter, means, methods, or steps, presently existing or later to be developed that perform substantially the same function or achieve substantially the same result as the corresponding embodiments described herein may be utilized according to the presently disclosed inventive concepts. Accordingly, the presently disclosed inventive concepts are intended to include within their scope all such processes, compositions of matter, means, methods, or steps.

What is claimed is:

1. A method of inhibiting activity of an anti-dopamine D1 receptor (D1R) antibody, the method comprising:
   obtaining a retro-inverso peptide consisting of the amino acid sequence SEQ ID NO:30; and
   exposing the retro-inverso peptide to the anti-D1R antibody, wherein the retro-inverso peptide binds to and reduces the activity of the anti-D1R antibody.

2. A method of inhibiting activity of an anti-dopamine D2 receptor (D2R) antibody, the method comprising:
   obtaining a retro-inverso peptide consisting of the amino acid sequence SEQ ID NO:31; and
   exposing the retro-inverso peptide to the anti-D2R antibody, wherein the retro-inverso peptide binds to and reduces the activity of the anti-D2R antibody.

* * * * *

UNITED STATES PATENT AND TRADEMARK OFFICE
CERTIFICATE OF CORRECTION

PATENT NO. : 10,899,822 B2
APPLICATION NO. : 16/697589
DATED : January 26, 2021
INVENTOR(S) : David C. Kem It is certified that error appears in the above-identified patent and that said Letters Patent is hereby corrected as shown below:

In the Specification

Column 21, Line 1: Delete "Ca'" and replace with -- $Ca^{2+}$ --

Column 22, Line 58: After "reproduce" delete "BAR" and replace with -- $\beta AR$ --

Column 23, Line 28: Before "adrenergic" delete "al" and replace with -- $\alpha 1$ --

Signed and Sealed this
Second Day of March, 2021

Drew Hirshfeld
*Performing the Functions and Duties of the*
*Under Secretary of Commerce for Intellectual Property and*
*Director of the United States Patent and Trademark Office*

```
                         SEQUENCE LISTING

<160> NUMBER OF SEQ ID NOS: 31

<210> SEQ ID NO 1
<211> LENGTH: 27
<212> TYPE: PRT
<213> ORGANISM: Homo sapiens

<400> SEQUENCE: 1

Ile His Arg Asn Val Phe Phe Ile Glu Asn Thr Asn Ile Thr Val Cys
1               5                   10                  15

Ala Phe His Tyr Glu Ser Gln Asn Ser Thr Leu
            20                  25

<210> SEQ ID NO 2
<211> LENGTH: 7
<212> TYPE: PRT
<213> ORGANISM: Homo sapiens

<400> SEQUENCE: 2

Ala Phe His Tyr Glu Ser Gln
1               5

<210> SEQ ID NO 3
<211> LENGTH: 27
<212> TYPE: PRT
<213> ORGANISM: Artificial sequence
<220> FEATURE:
<223> OTHER INFORMATION: Retro-inverso D-amino acid sequence of SEQ ID
      NO:2
<220> FEATURE:
<221> NAME/KEY: MISC_FEATURE
<222> LOCATION: (1)..(27)
<223> OTHER INFORMATION: all D-amino acids

<400> SEQUENCE: 3

Leu Thr Ser Asn Gln Ser Glu Tyr His Phe Ala Cys Val Thr Ile Asn
1               5                   10                  15

Thr Asn Glu Ile Phe Phe Val Asn Arg His Ile
            20                  25

<210> SEQ ID NO 4
<211> LENGTH: 7
<212> TYPE: PRT
<213> ORGANISM: Artificial sequence
<220> FEATURE:
<223> OTHER INFORMATION: Retro-inverso D-amino acid sequence of SEQ ID
      NO:2.
<220> FEATURE:
<221> NAME/KEY: MISC_FEATURE
<222> LOCATION: (1)..(7)
<223> OTHER INFORMATION: all D-amino acids

<400> SEQUENCE: 4
```

Gln Ser Glu Tyr His Phe Ala
1               5

<210> SEQ ID NO 5
<211> LENGTH: 13
<212> TYPE: PRT
<213> ORGANISM: Homo sapiens

<400> SEQUENCE: 5

Trp Gly Arg Trp Glu Tyr Gly Ser Phe Phe Cys Glu Leu
1               5                   10

<210> SEQ ID NO 6
<211> LENGTH: 26
<212> TYPE: PRT
<213> ORGANISM: Homo sapiens

<400> SEQUENCE: 6

His Trp Trp Arg Ala Glu Ser Asp Glu Ala Arg Arg Cys Tyr Asn Asp
1               5                   10                  15

Pro Lys Cys Cys Asp Phe Val Thr Asn Arg
            20                  25

<210> SEQ ID NO 7
<211> LENGTH: 11
<212> TYPE: PRT
<213> ORGANISM: Homo sapiens

<400> SEQUENCE: 7

Met Lys Met Trp Thr Phe Gly Asn Phe Trp Cys
1               5                   10

<210> SEQ ID NO 8
<211> LENGTH: 26
<212> TYPE: PRT
<213> ORGANISM: Homo sapiens

<400> SEQUENCE: 8

His Trp Tyr Arg Ala Thr His Gln Glu Ala Ile Asn Cys Tyr Ala Asn
1               5                   10                  15

Glu Thr Cys Cys Asp Phe Phe Thr Asn Gln
            20                  25

<210> SEQ ID NO 9
<211> LENGTH: 29
<212> TYPE: PRT
<213> ORGANISM: Homo sapiens

<400> SEQUENCE: 9

His Lys Ala Lys Pro Thr Ser Pro Ser Asp Gly Asn Ala Thr Ser Leu
1               5                   10                  15

Ala Glu Thr Ile Asp Asn Cys Asp Ser Ser Leu Ser Arg
            20                  25

<210> SEQ ID NO 10
<211> LENGTH: 16
<212> TYPE: PRT
<213> ORGANISM: Homo sapiens

<400> SEQUENCE: 10

Gly Leu Asn Asn Ala Asp Gln Asn Glu Cys Ile Ile Ala Asn Pro Ala
1               5                   10                  15

<210> SEQ ID NO 11
<211> LENGTH: 17
<212> TYPE: PRT
<213> ORGANISM: Homo sapiens

<400> SEQUENCE: 11

Thr Leu Tyr Thr Val Ile Gly Tyr Trp Pro Leu Gly Pro Val Val Cys
1               5                   10                  15

Asp

<210> SEQ ID NO 12
<211> LENGTH: 25
<212> TYPE: PRT
<213> ORGANISM: Homo sapiens

<400> SEQUENCE: 12

Val Arg Thr Val Glu Asp Gly Glu Cys Tyr Ile Gln Phe Phe Ser Asn
1               5                   10                  15

Ala Ala Val Thr Phe Gly Thr Ala Ile
            20                  25

<210> SEQ ID NO 13
<211> LENGTH: 17
<212> TYPE: PRT
<213> ORGANISM: Homo sapiens

<400> SEQUENCE: 13

Thr Thr Tyr Ile Ile Met Asn Arg Trp Ala Leu Gly Asn Leu Ala Cys
1               5                   10                  15

Asp

<210> SEQ ID NO 14
<211> LENGTH: 25
<212> TYPE: PRT
<213> ORGANISM: Homo sapiens

<400> SEQUENCE: 14

Lys Arg Thr Val Pro Pro Gly Glu Cys Phe Ile Gln Phe Leu Ser Glu
1               5                   10                  15

Pro Thr Ile Thr Phe Gly Thr Ala Ile
            20                  25

<210> SEQ ID NO 15
<211> LENGTH: 13
<212> TYPE: PRT
<213> ORGANISM: Homo sapiens

<400> SEQUENCE: 15

Tyr Trp Ala Phe Gly Arg Val Phe Cys Asn Ile Trp Ala
1               5                   10

<210> SEQ ID NO 16
<211> LENGTH: 25
<212> TYPE: PRT
<213> ORGANISM: Homo sapiens

<400> SEQUENCE: 16

Gly Trp Arg Gln Pro Ala Pro Glu Asp Glu Thr Ile Cys Gln Ile Asn
1               5                   10                  15

Glu Glu Pro Gly Tyr Val Leu Phe Ser
            20                  25

```
<210> SEQ ID NO 17
<211> LENGTH: 15
<212> TYPE: PRT
<213> ORGANISM: Homo sapiens

<400> SEQUENCE: 17

Thr Ala Met Glu Tyr Arg Trp Pro Phe Gly Asn Tyr Leu Cys Lys
1               5                   10                  15

<210> SEQ ID NO 18
<211> LENGTH: 29
<212> TYPE: PRT
<213> ORGANISM: Homo sapiens

<400> SEQUENCE: 18

Tyr Phe Arg Asp Val Arg Thr Ile Glu Tyr Leu Gly Val Asn Ala Cys
1               5                   10                  15

Ile Met Ala Phe Pro Pro Glu Lys Tyr Ala Gln Trp Ser
            20                  25

<210> SEQ ID NO 19
<211> LENGTH: 11
<212> TYPE: PRT
<213> ORGANISM: Artificial Sequence
<220> FEATURE:
<223> OTHER INFORMATION: Retro-inverso D-amino acid sequence of portion
      of SEQ ID NO:1
<220> FEATURE:
<221> NAME/KEY: MISC_FEATURE
<222> LOCATION: (1)..(1)
<223> OTHER INFORMATION: All D-amino acids

<400> SEQUENCE: 19

Ser Asn Gln Ser Glu Tyr His Phe Ala Cys Val
1               5                   10

<210> SEQ ID NO 20
<211> LENGTH: 27
<212> TYPE: PRT
<213> ORGANISM: Artificial sequence
<220> FEATURE:
<223> OTHER INFORMATION: Retro-inverso D-amino acid sequence of SEQ ID
      NO:1 with cyclic group
<220> FEATURE:
<221> NAME/KEY: MISC_FEATURE
<222> LOCATION: (1)..(1)
<223> OTHER INFORMATION: cyclo
<220> FEATURE:
<221> NAME/KEY: MISC_FEATURE
<222> LOCATION: (1)..(27)
<223> OTHER INFORMATION: all D-amino acids

<400> SEQUENCE: 20

Leu Thr Ser Asn Gln Ser Glu Tyr His Phe Ala Cys Val Thr Ile Asn
1               5                   10                  15

Thr Asn Glu Ile Phe Phe Val Asn Arg His Ile
            20                  25

<210> SEQ ID NO 21
<211> LENGTH: 9
<212> TYPE: PRT
<213> ORGANISM: Artificial sequence
<220> FEATURE:
<223> OTHER INFORMATION: Homo sapiens epitope with at least one D-amino
      acid on each end
<220> FEATURE:
<221> NAME/KEY: MISC_FEATURE
<222> LOCATION: (1)..(1)
<223> OTHER INFORMATION: at least one D-amino acid
```

```
<220> FEATURE:
<221> NAME/KEY: MISC_FEATURE
<222> LOCATION: (9)..(9)
<223> OTHER INFORMATION: at least one D-amino acid

<400> SEQUENCE: 21

Xaa Ala Phe His Tyr Glu Ser Gln Xaa
1               5

<210> SEQ ID NO 22
<211> LENGTH: 11
<212> TYPE: PRT
<213> ORGANISM: Artificial sequence
<220> FEATURE:
<223> OTHER INFORMATION: Homo sapiens epitope with at least one D-amino
      acid on each end.
<220> FEATURE:
<221> NAME/KEY: MISC_FEATURE
<222> LOCATION: (1)..(1)
<223> OTHER INFORMATION: at least one D-amino acid
<220> FEATURE:
<221> NAME/KEY: MISC_FEATURE
<222> LOCATION: (11)..(11)
<223> OTHER INFORMATION: at least one D-amino acid

<400> SEQUENCE: 22

Xaa His Trp Tyr Arg Ala Thr His Gln Glu Xaa
1               5                   10

<210> SEQ ID NO 23
<211> LENGTH: 8
<212> TYPE: PRT
<213> ORGANISM: Artificial sequence
<220> FEATURE:
<223> OTHER INFORMATION: Homo sapiens epitope with at least one D-amino
      acid on each end.
<220> FEATURE:
<221> NAME/KEY: MISC_FEATURE
<222> LOCATION: (1)..(1)
<223> OTHER INFORMATION: at least one D-amino acid
<220> FEATURE:
<221> NAME/KEY: MISC_FEATURE
<222> LOCATION: (8)..(8)
<223> OTHER INFORMATION: at least one D-amino acid

<400> SEQUENCE: 23

Xaa Tyr Trp Ala Phe Gly Arg Xaa
1               5

<210> SEQ ID NO 24
<211> LENGTH: 8
<212> TYPE: PRT
<213> ORGANISM: Artificial sequence
<220> FEATURE:
<223> OTHER INFORMATION: Homo sapiens with at least one D-amino acid on
      each end.
<220> FEATURE:
<221> NAME/KEY: MISC_FEATURE
<222> LOCATION: (1)..(1)
<223> OTHER INFORMATION: at least one D-amino acid
<220> FEATURE:
<221> NAME/KEY: MISC_FEATURE
<222> LOCATION: (8)..(8)
<223> OTHER INFORMATION: at least one D-amino acid

<400> SEQUENCE: 24

Xaa Ala Pro Glu Asp Glu Thr Xaa
1               5

<210> SEQ ID NO 25
<211> LENGTH: 11
```

```
<212> TYPE: PRT
<213> ORGANISM: Artificial Sequence
<220> FEATURE:
<223> OTHER INFORMATION: Homo sapiens epitope with two D-amino acids on
      each end.
<220> FEATURE:
<221> NAME/KEY: MISC_FEATURE
<222> LOCATION: (1)..(2)
<223> OTHER INFORMATION: D-amino acids
<220> FEATURE:
<221> NAME/KEY: MISC_FEATURE
<222> LOCATION: (10)..(11)
<223> OTHER INFORMATION: D-amino acids

<400> SEQUENCE: 25

Val Cys Ala Phe His Tyr Glu Ser Gln Asn Ser
1               5                   10

<210> SEQ ID NO 26
<211> LENGTH: 10
<212> TYPE: PRT
<213> ORGANISM: Homo sapiens

<400> SEQUENCE: 26

Arg Cys Tyr Asn Asp Pro Lys Cys Cys Asp
1               5                   10

<210> SEQ ID NO 27
<211> LENGTH: 10
<212> TYPE: PRT
<213> ORGANISM: Artificial sequence
<220> FEATURE:
<223> OTHER INFORMATION: Retro-inverso D-amino acid sequence of SEQ ID
      NO:25
<220> FEATURE:
<221> NAME/KEY: MISC_FEATURE
<222> LOCATION: (1)..(10)
<223> OTHER INFORMATION: All D-amino acids

<400> SEQUENCE: 27

Asp Cys Cys Lys Pro Asp Asn Tyr Cys Arg
1               5                   10

<210> SEQ ID NO 28
<211> LENGTH: 6
<212> TYPE: PRT
<213> ORGANISM: Homo sapiens

<400> SEQUENCE: 28

His Trp Tyr Arg Ala Thr
1               5

<210> SEQ ID NO 29
<211> LENGTH: 6
<212> TYPE: PRT
<213> ORGANISM: Artificial sequence
<220> FEATURE:
<223> OTHER INFORMATION: Retro-inverso D-amino acid sequence of SEQ ID
      NO:28
<220> FEATURE:
<221> NAME/KEY: MISC_FEATURE
<222> LOCATION: (1)..(6)
<223> OTHER INFORMATION: all D-amino acids

<400> SEQUENCE: 29

Thr Ala Arg Tyr Trp His
1               5

<210> SEQ ID NO 30
```

```
<211> LENGTH: 29
<212> TYPE: PRT
<213> ORGANISM: Artificial sequence
<220> FEATURE:
<223> OTHER INFORMATION: Retro-inverso D-amino acid sequence of SEQ ID
      NO:9

<400> SEQUENCE: 30

Arg Ser Leu Ser Ser Asp Cys Asn Asp Ile Thr Glu Ala Leu Ser Thr
1               5                   10                  15

Ala Asn Gly Asp Ser Pro Ser Thr Pro Lys Ala Lys His
            20                  25

<210> SEQ ID NO 31
<211> LENGTH: 16
<212> TYPE: PRT
<213> ORGANISM: Artificial sequence
<220> FEATURE:
<223> OTHER INFORMATION: Retro-inverso D-amino acid sequence of SEQ ID
      NO:10

<400> SEQUENCE: 31

Ala Pro Asn Ala Ile Ile Cys Glu Asn Gln Asp Ala Asn Asn Leu Gly
1               5                   10                  15
```